(12) United States Patent
Hussain et al.

(10) Patent No.: US 11,459,499 B2
(45) Date of Patent: Oct. 4, 2022

(54) AMIDOAMINE-BASED GEMINI SURFACTANT CONTAINING ETHOXYLATE UNITS AND A METHOD FOR OIL RECOVERY

(71) Applicant: King Fahd University of Petroleum and Minerals, Dhahran (SA)

(72) Inventors: Syed M. Shakil Hussain, Dhahran (SA); Muhammad Shahzad Kamal, Dhahran (SA)

(73) Assignee: King Fahd University of Petroleum and Minerals, Dhahran (SA)

( * ) Notice: Subject to any disclaimer, the term of this patent is extended or adjusted under 35 U.S.C. 154(b) by 0 days.

(21) Appl. No.: 16/585,908

(22) Filed: Sep. 27, 2019

(65) Prior Publication Data
US 2020/0181479 A1    Jun. 11, 2020

Related U.S. Application Data

(60) Provisional application No. 62/777,981, filed on Dec. 11, 2018.

(51) Int. Cl.
| | |
|---|---|
| *C09K 8/584* | (2006.01) |
| *B01F 17/00* | (2006.01) |
| *C09K 8/588* | (2006.01) |
| *C07C 235/10* | (2006.01) |
| *C09K 23/00* | (2022.01) |

(52) U.S. Cl.
CPC ............ *C09K 8/584* (2013.01); *C07C 235/10* (2013.01); *C09K 8/588* (2013.01); *C09K 23/00* (2022.01)

(58) Field of Classification Search
CPC .. A61K 38/465; A61K 48/005; C07C 235/10; C09K 23/00; C09K 8/584; C09K 8/588; C12N 15/102; C12N 2750/14143
See application file for complete search history.

(56) References Cited

U.S. PATENT DOCUMENTS 5,118,717 A    6/1992  Hodgdon et al.
10,093,846 B2  10/2018  Ghumare et al.
(Continued)

FOREIGN PATENT DOCUMENTS

CN    101869814 A    10/2010
CN    102114397 A  *  7/2011
(Continued)

OTHER PUBLICATIONS

CN 102114397A Bib (Year: 2011).*
(Continued)

*Primary Examiner* — Ellen M Mcavoy
*Assistant Examiner* — Chantel L Graham
(74) *Attorney, Agent, or Firm* — Oblon, McClelland, Maier & Neustadt, L.L.P.

(57) ABSTRACT

Amidoamine-based gemini surfactants having dual chains connected via an alkyl linker. Each chain contains a quaternary ammonium head group and an ethoxylated alkyl tail. Properties of the surfactant including thermal stability, critical micelle concentration, and foam stability are specified. A method of recovering oil from a reservoir using an aqueous composition that contains the surfactant and a polymer (e.g. AM-AMPS) is also provided. This method is particularly effective for oil recovery in reservoirs of high temperature and/or high salinity.

20 Claims, 11 Drawing Sheets

12-E1-12 (1a)
12-E2-12 (1b)

(56) References Cited

U.S. PATENT DOCUMENTS

2017/0081582 A1* 3/2017 Ghumare ................. C09K 8/74
2019/0233716 A1* 8/2019 Alexis ..................... C09K 8/588

FOREIGN PATENT DOCUMENTS

CN          102126972 B     2/2014
CN          106540631 B     3/2019

OTHER PUBLICATIONS

CN102114397A Translation Claims (Year: 2011).*
CN102114397A Translation Description (Year: 2011).*
Hussain, et al. ; Effect of the number of ethylene oxide units on the properties of synthesized tailor-made cationic gemini surfactants for oilfield applications ; Journal of Molecular Structure 1196 ; pp. 851-860 ; Jul. 4, 2019 ; 10 Pages.
Hussain, et al. ; Synthesis of Novel Ethoxylated Quaternary Ammonium Gemini Surfactants for Enhanced Oil Recovery Application ; MDPI energies ; May 8, 2019 ; 16 Pages.
Abd-Elaal, et al. ; Three Gemini cationic surfactants based on polyethylene glycol as effective corrosion inhibitor for mild steel in acidic environment; Journal of the Association of Arab Universities for Basic and Applied Sciences 24 ; pp. 54-65; Apr. 29, 2017; 12 Pages.

* cited by examiner

AMIDOAMINE-BASED GEMINI SURFACTANT CONTAINING ETHOXYLATE UNITS AND A METHOD FOR OIL RECOVERY

CROSS REFERENCE TO RELATED APPLICATIONS

This application claims the benefit of priority of U.S. Provisional Application No. 62/777,981 filed Dec. 11, 2018, the entire contents of which are herein incorporated by reference.

STATEMENT OF ACKNOWLEDGEMENT

The inventors acknowledge the support provided by the College of Petroleum Engineering & Geoscience of King Fand University of Petroleum and Minerals (KFUPM) through a collaborative project with The University of Texas at Austin.

STATEMENT REGARDING PRIOR DISCLOSURE BY THE INVENTORS

Aspects of this technology are described in an article "Effect of the number of ethylene oxide units on the properties of synthesized tailor-made cationic gemini surfactants for oilfield applications" published in J. Mol. Struct., 2019, 1196, 851-860, on Jul. 4, 2019, which is incorporated herein by reference in its entirety.

BACKGROUND OF THE INVENTION

Technical Field

The present disclosure relates to a gemini surfactant having two chains connected by an alkyl linker, whereby each chain contains a quaternary ammonium head group, ethoxylate units, and an alkyl tail. Additionally, the present disclosure relates to a method for oil recovery using a formulation containing the gemini surfactant and a polymer.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Surfactants are used for a diverse range of oilfield applications including well stimulation [W. Al-Sadat, M. Nasser, F. Chang, H. Nasr-El-Din, I. Hussein, Rheology of a viscoelastic zwitterionic surfactant used in acid stimulation: Effects of surfactant and electrolyte concentration, Journal of Petroleum Science and Engineering, 124 (2014) 341-349], water and oil based fluid for drilling [M. El-Sukkary, F. Ghuiba, G. Sayed, M. Abdou, E. Badr, S. Tawfik, N. Negm, Evaluation of some vanillin-modified polyoxyethylene surfactants as additives for water based mud, Egyptian Journal of Petroleum, 23 (2014) 7-14; and G. Zhuang, H. Zhang, H. Wu, Z. Zhang, L. Liao, Influence of the surfactants' nature on the structure and rheology of organo-montmorillonite in oil-based drilling fluids, Applied Clay Science, 135 (2017) 244-252], refining [A. M. Atta, M. M. Abdullah, H. A. Al-Lohedan, A. O. Ezzat, Demulsification of heavy crude oil using new nonionic cardanol surfactants, Journal of Molecular Liquids, 252 (2018) 311-320], completion [A. Audibert-Hayet, C. Dalmazzone, Surfactant system for water-based well fluids, Colloids and Surfaces A: Physicochemical and Engineering Aspects, 288 (2006) 113-120], corrosion inhibitor [M. Migahed, M. EL-Rabiei, H. Nady, E. Zaki, Novel Gemini cationic surfactants as anti-corrosion for X-65 steel dissolution in oilfield produced water under sweet conditions: Combined experimental and computational investigations, Journal of Molecular Structure, 1159 (2018) 10-22], water shutoff [Y. Qing, W. Yefei, Z. Wei, Q. Ziyuan, Z. Fulin, Study and application of gelled foam for in-depth water shutoff in a fractured oil reservoir, Journal of Canadian Petroleum Technology, 48 (2009) 51-55], fluid loss additive [M. J. Miller, M. Samuel, P. S. Vinod, T. N. Olsen, Compositions and methods to control fluid loss in surfactant-based wellbore service fluids, U.S. Pat. No. 6,605,570 B2], and enhanced oil recovery [C. Negin, S. Ali, Q. Xie, Most common surfactants employed in chemical enhanced oil recovery, Petroleum, 3 (2017) 197-211]. Surfactants can act as emulsifiers, demulsifiers, interfacial tension (IFT) reducers, dispersants, wettability modifier, foaming and wetting agents [R. Sharma, A. Kamal, M. Abdinejad, R. K. Mahajan, H. -B. Kraatz, Advances in the synthesis, molecular architectures and potential applications of gemini surfactants, Advances in colloid and interface science, 248 (2017) 35-68].

Gemini surfactants have a dimeric molecular structure containing two hydrophilic head groups and two hydrophobic tails that are covalently bonded via spacer groups [F. M. Menger, J. S. Keiper, Gemini surfactants, Angewandte Chemie International Edition, 39 (2000) 1906-1920, incorporated herein by reference in its entirety]. Compared to conventional surfactants having one hydrophilic group and one hydrophobic group, gemini surfactants have demonstrated improved physicochemical properties including minimum critical micelle concentration (CMC), low IFT, good solubility, and better foaming and wetting properties [T. Tian, Q. Kang, T. Wang, J. Xiao, L. Yu, Alignment of nematic liquid crystals decorated with gemini surfactants and interaction of proteins with gemini surfactants at fluid interfaces, Journal of colloid and interface science, 518 (2018) 111-121, incorporated herein by reference in its entirety]. For instance, the reported CMC of a gemini surfactant "12-2-12" was about $5.5 \times 10^{-2}$ wt. %, which is much smaller than that of its single-chain counter-part dodecyltrimethylammonium bromide (DTAB), $5.0 \times 10^{-1}$ wt. % [T. Lu, Y. Lan, C. Liu, J. Huang, Y. Wang, Surface properties, aggregation behavior and micellization thermodynamics of a class of gemini surfactants with ethyl ammonium headgroups, J. Colloid Interface Sci., 377 (2012) 222-230, incorporated herein by reference in its entirety].

In the last decades, the preparation and application of cationic gemini surfactants containing ammonium head groups and alkyl chains of various lengths have been reported in the literature [K. Taleb, M. Mohamed-Benkada, N. Benhamed, S. Saidi-Besbes, Y. Grohens, A. Derdour, Benzene ring containing cationic gemini surfactants: Synthesis, surface properties and antibacterial activity, J. Mol. Liq., 241 (2017) 81-90, incorporated herein by reference in its entirety]. Injection of ineffective surfactants into the reservoir can cause excessive adsorption and thus decrease oil recovery. Selection of suitable moieties to be incorporated into the framework of a surfactant may improve its physicochemical properties and oil recovery performance.

In view of the forgoing, one objective of the present disclosure is to provide a family of gemini surfactants exhibiting good water solubility, high tolerance for salinity, and satisfactory thermal stability. Another objective of the present disclosure is to provide a method of recovering hydrocarbons from an oil reservoir using a composition including an aqueous solution and an oil recovery formulation that contains the gemini surfactant and a polymer.

BRIEF SUMMARY OF THE INVENTION

According to a first aspect, the present disclosure relates to a surfactant of formula (I)

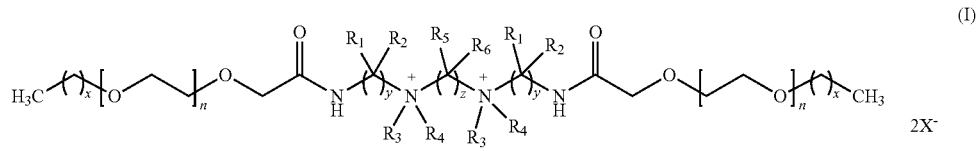

(I)

or a solvate thereof, a tautomer thereof, a stereoisomer thereof, or a mixture thereof, wherein (i) each of $R_1$ and $R_2$, and $R_5$ and $R_6$ are independently selected from the group consisting of a hydrogen, an optionally substituted alkyl, and an optionally substituted cycloalkyl, (ii) each of $R_3$ and $R_4$ are independently selected from the group consisting of an optionally substituted alkyl, and an optionally substituted cycloalkyl, (iii) each of n is an integer in a range of 1-15, (iv) each of x is an integer in a range of 5-21, (v) each of y is an integer in a range of 2-5, (vi) z is an integer in a range of 4-12, and (vii) X is an anion selected from the group consisting of a halide ion, a hexafluorophosphate ion, a trifluoromethanesulfonate ion, and a tetrafluoroborate ion.

In one embodiment, each of $R_1$ and $R_2$ are independently a hydrogen, or a methyl.

In one embodiment, each of $R_1$ and $R_2$ are a hydrogen.

In one embodiment, each of $R_3$ and $R_4$ are independently selected from the group consisting of a methyl, an ethyl, and an isopropyl.

In one embodiment, each of $R_3$ and $R_4$ are a methyl.

In one embodiment, $R_5$ and $R_6$ are independently a hydrogen, or a methyl.

In one embodiment, $R_5$ and $R_6$ are a hydrogen.

In one embodiment, each of n is an integer in a range of 2-11.

In one embodiment, each of x is an integer in a range of 11-13.

In one embodiment, each of y is 3.

In one embodiment, z is 6.

In one embodiment, X is bromide.

In one embodiment, the surfactant has a formula (II)

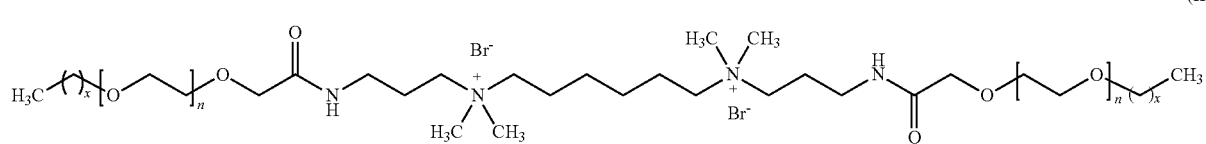

(II)

wherein each of n is an integer in a range of 2-11, and each of x is an integer in a range of 11-13.

In one embodiment, the surfactant has a critical micelle concentration of $2\times10^{-5}$ to $1\times10^{-4}$ mol/L in saline having a salinity of 10,000 ppm to 400,000 ppm at a temperature of 20-70° C.

According to a second aspect, the present disclosure relates to a method of recovering hydrocarbons from a reservoir. The method involves the steps of injecting a composition comprising an aqueous solution and an oil recovery formulation into the reservoir, and collecting hydrocarbons from the reservoir, wherein the oil recovery formulation contains the surfactant of formula (I) of the first aspect, and a copolymer comprising reacted units of acrylamide and 2-acrylamido-2-methylpropane sulfonic acid.

In one embodiment, the copolymer has a molar ratio of acrylamide to 2-acrylamido-2-methylpropane sulfonic acid in a range of 1:10 to 10:1, and a mass average molecular weight in a range of 1,000-20,000 kDa.

In one embodiment, the surfactant has the formula (II)

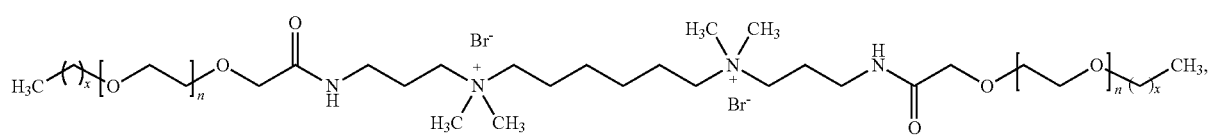

(II)

where each of n is an integer in a range of 6-11, and each of x is an integer in a range of 11-13.

In one embodiment, the surfactant of formula (I) is present in an amount of 0.01-0.2 wt % relative to a total weight of the composition.

In one embodiment, the reservoir has a temperature of 50-310° C.

In one embodiment, the aqueous solution is saline having a salinity of 10,000 ppm to 400,000 ppm.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
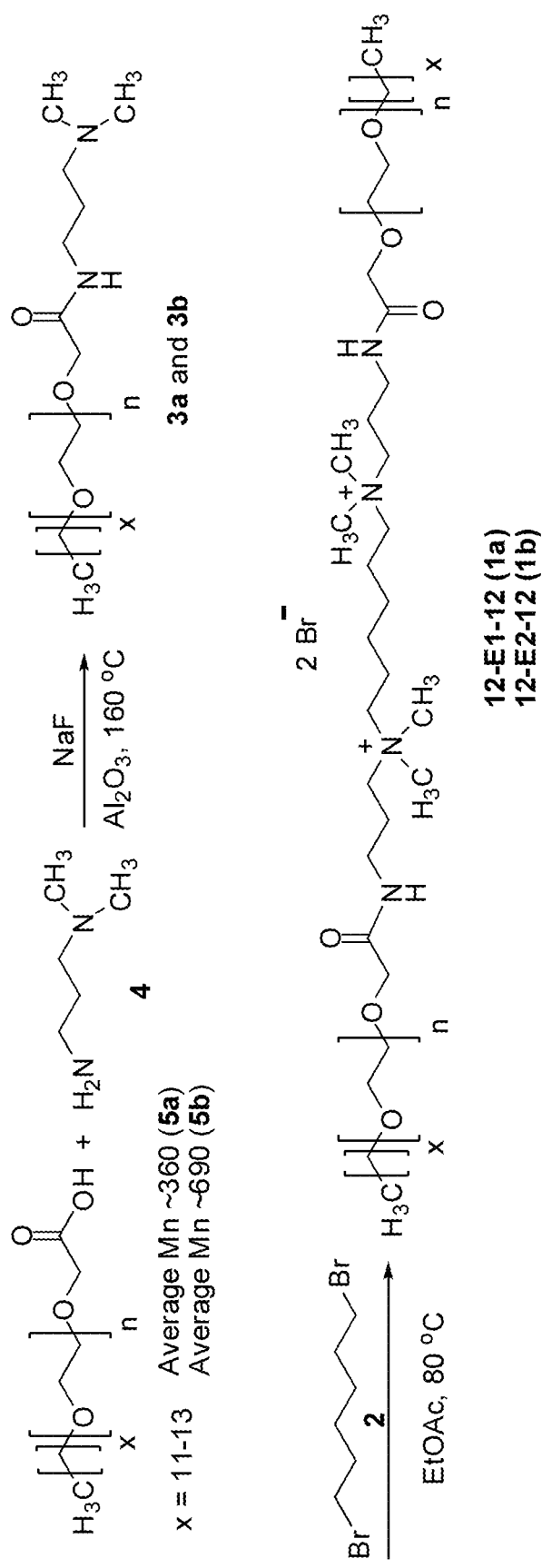
FIG. 1 is a synthetic scheme for the preparation of surfactants 12-E1-12 and 12-E2-12 from carboxylic acids having a number average molecular weight of about 360 g/mol, and about 690 g/mol, respectively, as well as 3-(dimethylamino)-1-propylamine and 1,6-dibromohexane.

Embodiments of the present disclosure will now be described more fully hereinafter with reference to the accompanying drawings, in which some, but not all embodiments of the disclosure are shown.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the words "about" or "substantially similar" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), or +/−15% of the stated value (or range of values).

As used herein, the terms "compound", "surfactant", and "product" are used interchangeably, and are intended to refer to a chemical entity, whether in the solid, liquid or gaseous phase, and whether in a crude mixture or purified and isolated.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, iso-butanol, tent-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those skilled in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the ring systems, stereogenic centers, and the like can all be present in the compounds, and all such stable isomers are contemplated in the present disclosure. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

As used herein, the term "alkyl" unless otherwise specified refers to both branched and straight chain saturated aliphatic primary, secondary, and/or tertiary hydrocarbons of typically $C_1$ to $C_{21}$, for example $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl.

The term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "halide", as used herein, means fluoride, chloride, bromide, and iodide.

The term "halogen", as used herein, means fluoro, chloro, bromo and iodo.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, unsubstituted amide (i.e. —CONH$_2$), substituted amide (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof. The substituents may themselves be optionally substituted, and may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

The present disclosure is intended to include all isotopes of atoms occurring in the present compounds. Isotopes include those atoms having the same atomic number but different mass numbers. By way of general example, and without limitation, isotopes of hydrogen include deuterium and tritium, isotopes of carbon include $^{13}C$ and $^{14}C$, isotopes of nitrogen include $^{14}N$ and $^{15}N$, and isotopes of oxygen include $^{16}O$, $^{17}O$ and $^{18}O$. Isotopically labeled compounds of the disclosure can generally be prepared by conventional techniques known to those of ordinary skill in the art or by processes and methods analogous to those described herein, using an appropriate isotopically labeled reagent in place of the non-labeled reagent otherwise employed.

According to a first aspect, the present disclosure relates to a surfactant of formula (I)

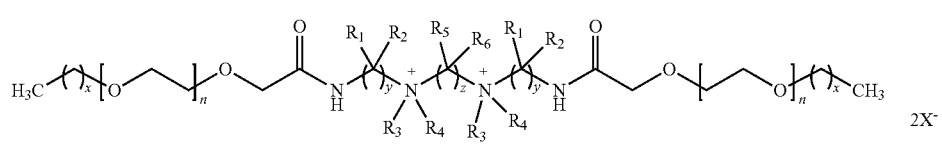

(I)

or a solvate thereof, a tautomer thereof, a stereoisomer thereof, or a mixture thereof. Gemini surfactants (or dimeric surfactants) have two hydrophilic groups and two hydrophobic groups in one molecule, in contrast to conventional surfactants that generally have a single hydrophilic group and a single hydrophobic group in one molecule. Gemini surfactants may be anionic, cationic, nonionic, or amphoteric. In one embodiment, the surfactant of formula (I) is a gemini surfactant.

Each of $R_1$ and $R_2$ are independently selected from the group consisting of a hydrogen, an optionally substituted alkyl, and an optionally substituted cycloalkyl. In one or more embodiments, each of $R_1$ and $R_2$ are independently a hydrogen, or a methyl. In one embodiment, each of $R_1$ and $R_2$ are the same. In another embodiment, each of $R_1$ and $R_2$ are different. In a preferred embodiment, each of $R_1$ and $R_2$ are a hydrogen.

Each of $R_3$ and $R_4$ are independently selected from the group consisting of an optionally substituted alkyl, and an optionally substituted cycloalkyl. Preferably, each of $R_3$ and $R_4$ are independently an optionally substituted $C_{1-6}$ alkyl, an optionally substituted $C_{2-5}$ alkyl, or an optionally substituted $C_{3-4}$ alkyl. In one or more embodiments, each of $R_3$ and $R_4$ are independently selected from the group consisting of a methyl, an ethyl, and an isopropyl. In a preferred embodiment, each of $R_3$ and $R_4$ are a methyl.

$R_5$ and $R_6$ are independently selected from the group consisting of a hydrogen, an optionally substituted alkyl, and an optionally substituted cycloalkyl. In one or more embodiments, $R_5$ and $R_6$ are independently a hydrogen, or a methyl. In one embodiment, $R_5$ and $R_6$ are the same. In another embodiment, $R_5$ and $R_6$ are different. In a preferred embodiment, $R_5$ and $R_6$ are a hydrogen.

As used herein, the value of x denotes an alkyl chain of —$CH_2$— groups connected to the —$CH_3$ end group of the surfactant of formula (I). In one or more embodiments, each of x is an integer in a range of 5-21, preferably 7-20, preferably 9-19, preferably 11-18, preferably 13-17, preferably 15-16. Most preferably, each of x is an integer in a range of 11-13.

As used herein, the value of y denotes an alkyl chain of —$C(R_1)(R_2)$— groups of the surfactant of formula (I). In one or more embodiments, each of y is an integer in a range of 2-5, preferably 3-4. Most preferably, each of y is 3.

As used herein, the value of z denotes an alkyl chain of —$C(R_5)(R_6)$— groups of the surfactant of formula (I). In one or more embodiments, z is an integer in a range of 4-12, preferably 5-11, preferably 6-10, preferably 7-9, or 8. Most preferably, z is 6.

Surface and thermal behaviors of a surfactant may be modified by changing the number of ethylene oxide groups present in the surfactant structure [J. Penfold, R. K. Thomas, P. Li, J. T. Petkov, I. Tucker, A. R. Cox, N. Hedges, J. R. Webster, M. W. Skoda, Impact of the degree of ethoxylation of the ethoxylated polysorbate nonionic surfactant on the surface self-assembly of hydrophobin-ethoxylated polysorbate surfactant mixtures, Langmuir, 30 (2014) 9741-9751, incorporated herein by reference in its entirety]. A surfactant incorporated with a proper number of ethylene oxide (EO) groups may demonstrate enhanced solubility and low interfacial tension (IFT) in the absence of a co-solvent such as methanol [C. Negin, S. Ali, Q. Xie, Most common surfactants employed in chemical enhanced oil recovery, Petroleum, 3 (2017) 197-211, incorporated herein by reference in its entirety]. Low IFT values may be attributed to the hydrogen bonding interaction between ether oxygen atom of EO units and hydrogen atoms of water molecules. Such intermolecular interactions promote the surfactant to adsorb at the interface between aqueous and oil, which leads to increased water solubility and reduced IFT [D. Levitt, S. Dufour, G. A. Pope, D. C. Morel, P. R. Gauer, Design of an ASP flood in a high-temperature, high-salinity, low-permeability carbonate, International Petroleum Technology Conference, International Petroleum Technology Conference, 2011, incorporated herein by reference in its entirety].

As used herein, the value of n denotes the degree of ethoxylation (—$OC_2H_4$—) of the surfactant of formula (I). In one or more embodiments, each of n is an integer in a range of 1-15, preferably 2-14, preferably 3-13, preferably 4-12, preferably 5-11, preferably 6-10, preferably 7-9. In a preferred embodiment, each of n is an integer in a range of 2-11, 4-9, or 6-8. Most preferably, each of n is in a range of 6-11, 7-10, or 8-9. It is equally envisaged that the surfactant disclosed herein may have values for each of x, y, n, and/or z that fall outside of the aforementioned preferred ranges and still provide suitable surfactants of formula (I).

The term "anion" means a negatively charged ion including, but not limited to, halides, such as fluoride, chloride, bromide, and iodide, nitrate, sulfate, phosphate, methanesulfonate, ethanesulfonate, p-toluenesulfonate, salicylate, malate, maleate, succinate, tartrate, citrate, acetate, perchlorate, trifluoromethanesulfonate, acetylacetonate, tetrafluoroborate, hexafluorophosphate, and hexafluoroacetylacetonate. In one embodiment, X of the surfactant of formula (I) is an anion selected from the group consisting of a halide ion, a hexafluorophosphate ion, a trifluoromethanesulfonate ion, and a tetrafluoroborate ion. In a preferred embodiment, X is halide, such as chloride, bromide, fluoride, and iodide. Most preferably, X is bromide.

In one or more embodiments, the surfactant disclosed herein has a formula (II)

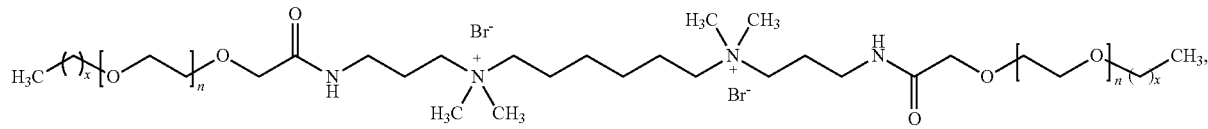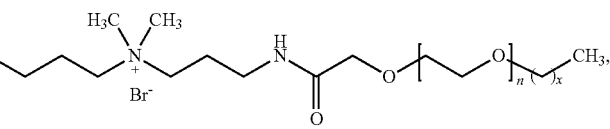

(II)

where each of n is an integer in a range of 1-15, preferably 2-14, preferably 3-13, preferably 4-12, preferably 5-11, preferably 6-10, preferably 7-9, or 8, and each of x is an integer in a range of 5-21, preferably 7-20, preferably 9-19, preferably 11-18, preferably 13-17, preferably 15-16. Most preferably, each of n is an integer in a range of 6-11, 7-10, or 8-9. For example, each of n is 9, 10, or 11. In a related embodiment, each of x is an integer in a range of 11-13, or 12.

In one embodiment, the surfactant of the present disclosure has a number average molecular weight (Mn) of up to 6,000 g/mol, preferably 600-5,500 g/mol, preferably 650-5,000 g/mol, preferably 700-4,000 g/mol, preferably 800-3,500 g/mol, preferably 900-3,000 g/mol, preferably 1,000-2,750 g/mol, preferably 1,200-2,500 g/mol, preferably 1,500-2,000 g/mol.

The surfactant of formula (I) may be prepared via a method depicted by FIG. 1. Specifically, the method may involve mixing a carboxylic acid of formula (III)

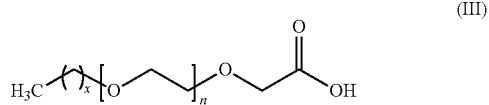

(III)

or a salt thereof, a solvate thereof, or a mixture thereof with an amine of formula (IV)

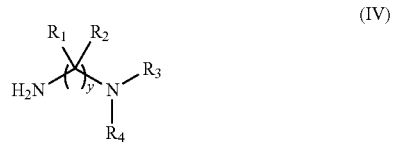

(IV)

or a salt thereof, a solvate thereof, a stereoisomer thereof, or a mixture thereof in the presence of a fluoride salt to form a mixture, heating the mixture to obtain an amidoamine intermediate, and reacting the amidoamine intermediate with a disubstituted alkyl compound of formula (V)

(V)

or a solvate thereof, a stereoisomer thereof, or a mixture thereof in a solvent, thereby forming the surfactant, wherein (i) $R_1$ and $R_2$, and $R_5$ and $R_6$ are independently from the group consisting of a hydrogen, an optionally substituted alkyl, and an optionally substituted cycloalkyl, (ii) $R_3$ and $R_4$ are independently selected from the group consisting of an optionally substituted alkyl, and an optionally substituted cycloalkyl, (iii) n is an integer in a range of 1-15, (iv) x is an integer in a range of 5-21, (v) y is an integer in a range of 2-5, (vi) z is an integer in a range of 4-12, and (vii) Y is a halogen.

In one or more embodiments, x of the carboxylic acid of formula (III) is an integer in a range of 5-21, preferably 7-20, preferably 9-19, preferably 11-18, preferably 13-17, preferably 15-16. Most preferably, x is an integer in a range of 11-13. In related embodiments, n of the carboxylic acid of formula (III) is an integer in a range of 1-15, preferably 2-14, preferably 3-13, preferably 4-12, preferably 5-11, preferably 6-10, preferably 7-9. In a preferred embodiment, n is an integer in a range of 2-11, 4-9, or 6-8. Most preferably, n is in a range of 6-11, 7-10, or 8-9.

Exemplary carboxylic acids that may be used herein include, but are not limited to, glycolic acid ethoxylate lauryl ether, glycolic acid ethoxylate hexyl ether, glycolic acid ethoxylate heptyl ether, glycolic acid ethoxylate octyl ether, glycolic acid ethoxylate nonyl ether, glycolic acid ethoxylate decyl ether, glycolic acid ethoxylate tetradecyl ether, glycolic acid ethoxylate hexadecyl ether, glycolic acid ethoxylate stearyl ether, glycolic acid ethoxylate nonadecyl ether, glycolic acid ethoxylate eicosyl ether, and glycolic acid ethoxylate heneicosyl ether. In one or more embodiments, the carboxylic acid of formula (III) has a number average molecular weight of 250-900 g/mol, preferably 300-850 g/mol, preferably 350-800 g/mol, preferably 400-750 g/mol, preferably 450-700 g/mol, preferably 500-650 g/mol, preferably 550-600 g/mol. In one embodiment, the carboxylic acid is glycolic acid ethoxylate lauryl ether with a number average molecular weight of about 360 g/mol. In a most preferred embodiment, the carboxylic acid is glycolic acid ethoxylate lauryl ether with a number average molecular weight of about 690 g/mol.

In one or more embodiments, $R_1$ and $R_2$ of the amine of formula (IV) are independently selected from the group consisting of a hydrogen and a methyl. In a preferred embodiment, $R_1$ and $R_2$ are a hydrogen. In a related embodiment, $R_3$ and $R_4$ of the amine of formula (IV) are independently selected from the group consisting of a methyl, an ethyl, and an isopropyl. In a preferred embodiment, $R_3$ and $R_4$ are a methyl. In another related embodiment, y of the amine of formula (IV) is an integer in a range of 2-5, preferably 3-4. In a preferred embodiment, y is 3. In a most preferred embodiment, the amine of formula of (IV) is 3-(dimethylamino)-1-propylamine. Other amines that may be used in addition to or in lieu of 3-(dimethylamino)-1-propylamine include, but are not limited to, 2-(dimethylamino)ethylamine, 2-(diethylamino)ethylamine, 1-dimethylamino-2-propylamine, 3-(diethylamino)propylamine, (3-amino-2-methylpropyl)dimethylamine, (3-amino-1-methylpropyl)dimethylamine, N,N,2,2-tetramethyl-1,3-propanediamine, 4-(dimethylamino)butylamine, 5-(dimethylamino)amylamine, 5-(diethylamino)pentylamine, and 5-(diisopropylamino)amylamine.

The method of the present disclosure may involve an amidation reaction of the mixture comprising the carboxylic acid of formula (III) and the amine of formula (IV) to produce a corresponding amidoamine intermediate of formula (VI)

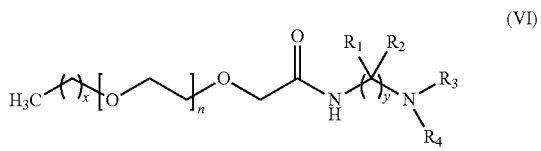

(VI)

or a salt thereof, a solvate thereof, a stereoisomer thereof, or a mixture thereof, wherein values for x and n are consistent with those described for the carboxylic acid of formula (III), and $R_1$, $R_2$, $R_3$, and $R_4$, as well as value for y are consistent with those described for the amine of formula (IV).

In a preferred embodiment, reacting the mixture comprising the carboxylic acid of formula (III) with the amine of formula (IV) is conducted in neat (solvent-free) condition. It is equally envisaged that the reaction may be adapted to be performed in a solvent such as benzene, xylene, dimethylformamide, tetrahydrofuran, ethyl acetate, diethyl ether, acetonitrile, dimethyl sulfoxide, methylene chloride, chloroform, nitrobenzene, isopropanol, and mixtures thereof. In a preferred embodiment, a molar ratio of the amine of formula (IV) to the carboxylic acid of formula (III) is in a range of 1:1 to 5:1, preferably 1:2 to 1:4, or about 2:7. In a preferred embodiment, the amine is introduced to the mixture in a two-stage or multi-stage fashion. For example, a first portion of the amine which is 50-70%, 55-65%, or about 57% of a total mole of the amine used herein may be added to the mixture and allowed to react with the carboxylic acid for 3-9 hours, 5-7 hours, or about 6 hours, and subsequently a second portion of the amine which is 30-50%, 35-45%, or about 43% of a total mole of the amine used herein may be added to the same mixture and allowed to react with the carboxylic acid for 2-8 hours, 4-6 hours, or about 5 hours. Alternatively, the amine may be introduced to the mixture in one batch and allowed to react with the carboxylic acid for 5-20 hours, 8-15 hours, or about 12 hours. In one or more embodiments, the aforementioned mixture is heated at a temperature of 50-200° C., preferably 100-190° C., preferably 120-180° C., preferably 130-170° C., preferably 150-160° C. under agitation. An external heat source, such as an oil bath, an oven, microwave, or a heating mantle, may be employed to heat the mixture. The mixture may be agitated throughout the duration of the reaction by employing a rotary shaker, a magnetic stirrer, or an overhead stirrer. In another embodiment, the mixture is left to stand (i.e. not agitated). In one embodiment, the mixture is sonicated in an ultrasonic bath or with an ultrasonic probe. The amidation reaction may be conducted in inert gas (e.g. nitrogen, argon, helium). Also, in some embodiments, the reaction may not be conducted in inert gas, but in a vacuum. In a preferred embodiment, the intermediate of formula (VI) is collected as an oil that may be separated and washed in acetone, ethyl acetate, and/or isopropanol and then dried. In one embodiment, the oil may be dried under vacuum until a constant weight is achieved. In a preferred embodiment, the step forming the intermediate of formula (VI) has a product yield of at least 75%, preferably at least 80%, preferably at least 90%, preferably at least 92%, preferably at least 94%, preferably at least 96%, preferably at least 97%.

In one or more embodiments, the mixture comprises a fluoride salt. The fluoride salt may be present as a catalyst to accelerate the amidation reaction. In a preferred embodiment, the fluoride salt used herein is at least one selected from the group consisting of sodium fluoride, potassium fluoride, silver fluoride, cesium fluoride, and tetrabutylammonium fluoride. In a most preferred embodiment, the fluoride salt is sodium fluoride. In one or more embodiments, a molar ratio of the fluoride salt to the carboxylic acid is in the range of 1:5 to 1:20, preferably 1:6 to 1:18, preferably 1:8 to 1:15, preferably 1:9 to 1:12, or about 1:10. Other amide bond formation reagents and catalysts that may be used in addition to or in lieu of the fluoride salt include, but are not limited to, carbodiimides such as 1-ethyl-3-(3-dimethylaminopropyl)carbodiimide (EDC), N,N'-dicyclohexylcarbodiimide (DCC), 1H-benzotriazole derivatives such as 1-[bis(dimethylamino)methylene]-1H-1,2,3-triazolo [4,5-b]pyridinium 3-oxid hexafluorophosphate (HATU), O-(benzotriazol-1-yl)-1,1,3,3-tetramethyluronium hexafluorophosphate (HBTU), O-benzotriazol-1-yl-1,1,3,3-tetramethyluronium tetrafluoroborate (TBTU), as well as phosphoric acid, sulfuric acid, boric acid, silica gel, and zeolite.

In one or more embodiments, the mixture further comprises a molecular sieve. The molecular sieve may facilitate the removal of by-product water produced during the amidation reaction. Non-limiting exemplary molecular sieves applicable to the method disclosed herein include aluminosilicate minerals, porous glass, activated carbon, clay, and mesoporous silica. In a preferred embodiment, the molecular sieve comprises aluminum oxide ($Al_2O_3$). In a most preferred embodiment, the molecular sieve comprises microporous aluminum oxide having an average pore size of 0.2-0.5 nm, or 0.3-0.4 nm. Other drying agents that may be used in addition to or in lieu of the molecular sieve include, but are not limited to zeolites, anhydrous sodium sulfate, anhydrous magnesium sulfate, anhydrous calcium chloride, and anhydrous calcium sulfate. Conventional water removing apparatus such as Dean-Stark trap may be utilized in addition to the aforementioned drying agents.

In one or more embodiments, z of the disubstituted alkyl of formula (V) is an integer in a range of 4-12, preferably 5-11, preferably 6-10, preferably 7-9, or 8. Most preferably, z is 6. In one embodiment, Y is a halogen, preferably a chloro, a bromo, or an iodo. Most preferably, Y is a bromo. In a most preferred embodiment, the disubstituted alkyl of formula (V) is 1,6-dibromohexane.

The method disclosed herein also involves reacting the intermediate of formula (VI) with the disubstituted alkyl of formula (V), thereby producing the surfactant of the first aspect. In a preferred embodiment, reacting the intermediate with the disubstituted alkyl is conducted in a polar protic solvent, preferably in ethanol. Exemplary polar protic solvents that may be used in addition to or in lieu of ethanol include methanol, n-propanol, isopropyl alcohol, n-butanol, and mixtures thereof. It is equally envisaged that the reaction may be adapted to be performed in polar aprotic solvent such as ethyl acetate, dimethylformamide, tetrahydrofuran, acetone, acetonitrile, and dimethyl sulfoxide. In certain embodiments, reacting the intermediate with the disubstituted alkyl is conducted without a solvent.

In a preferred embodiment, the reacting is performed at a concentration of the disubstituted alkyl in a range of 0.01-10 M, preferably 0.05-5 M, preferably 0.1-2 M, preferably 0.8-1.2 M. In a preferred embodiment, a molar ratio of the intermediate to the disubstituted alkyl is in a range of 1.5:1 to 5:1, preferably 2:1 to 4:1, or about 2.5:1. In a preferred embodiment, the aforementioned reacting is conducted under agitation at a temperature of up to 120° C., preferably 50-100° C., preferably 60-95° C., preferably 70-90° C., preferably 75-85° C., or about 80° C. and has a reaction time of up to 96 hours, preferably 6-72 hours, preferably 12-60 hours, preferably 30-54 hours, or about 48 hours. The surfactant may be isolated and purified from the reaction mixture by methods known to those of ordinary skill in the art such as distillation, crystallization, column chromatography, and high pressure liquid chromatography (HPLC) (normal phase or reversed phase). Preferred methods include, purifying the reaction mixture with column chromatography (with silica or alumina as the stationary phase), preparative thin layer chromatography, and recrystallization. In one embodiment, the surfactant is purified with a silica gel column. In a preferred embodiment, the step forming the surfactant has a product yield of at least 80%, preferably at least 85%, preferably at least 87%, preferably at least 90%, preferably at least 92%, preferably at least 95%.

The method disclosed herein may further involve an ion-exchange reaction when X is an anion other than a halide ion. For example, after reacting the intermediate with the disubstituted alkyl of formula (V), the product obtained may be subjected to an ion-exchange reaction with desirable salts comprising X anions such as hexafluorophosphate ions, trifluoromethanesulfonate ions, and tetrafluoroborate ions using methods known to those of ordinary skill in the art.

Figure 3:
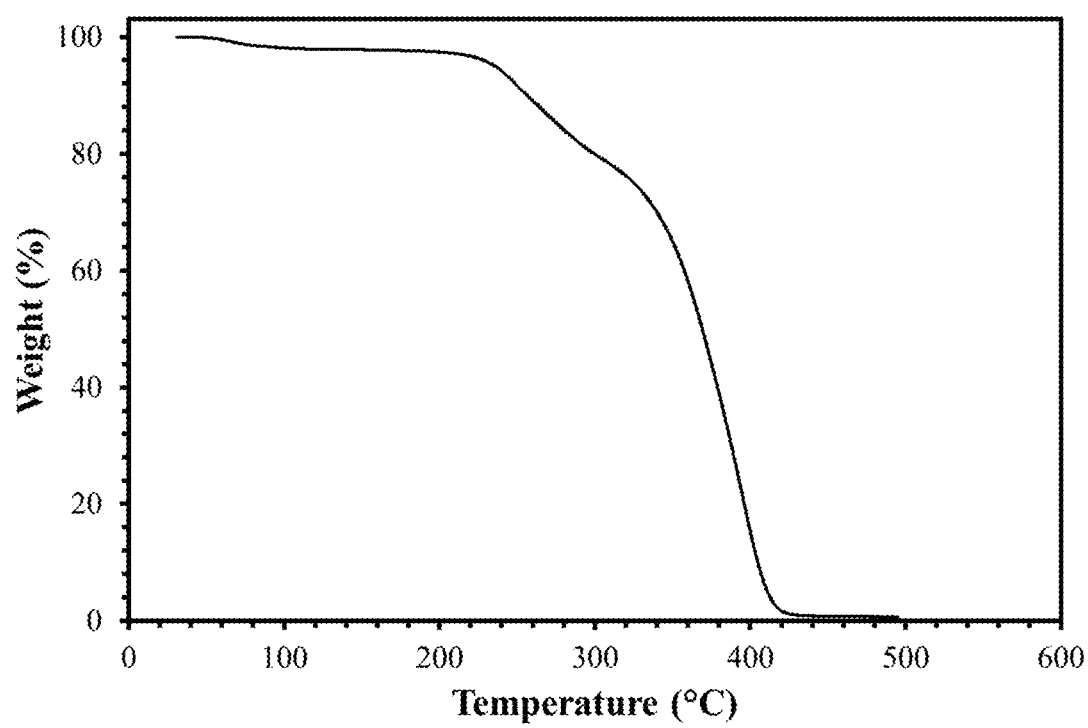
FIG. 3 is a thermal gravimetric analysis (TGA) curve of surfactant 12-E2-12.
Figure 4:
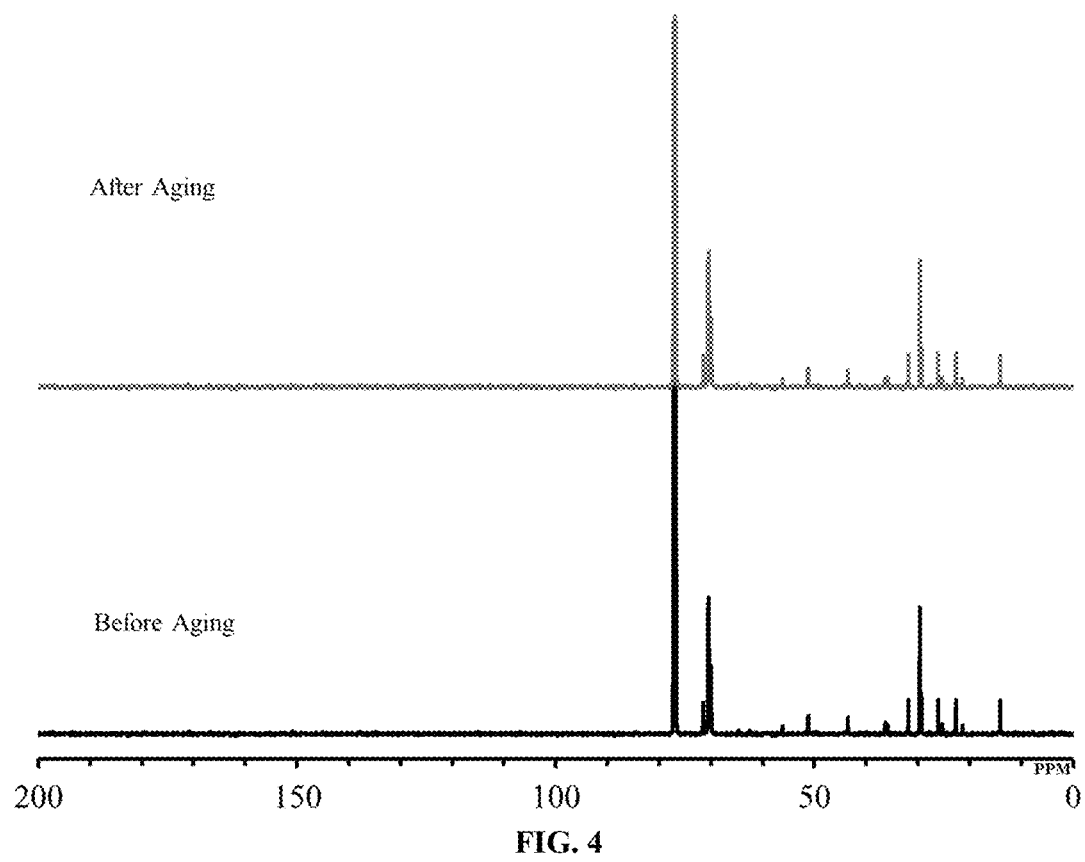
FIG. 4 is an overlay of $^{13}C$ NMR spectra of surfactant 12-E2-12 before and after aging at 90° C.
Figure 5:
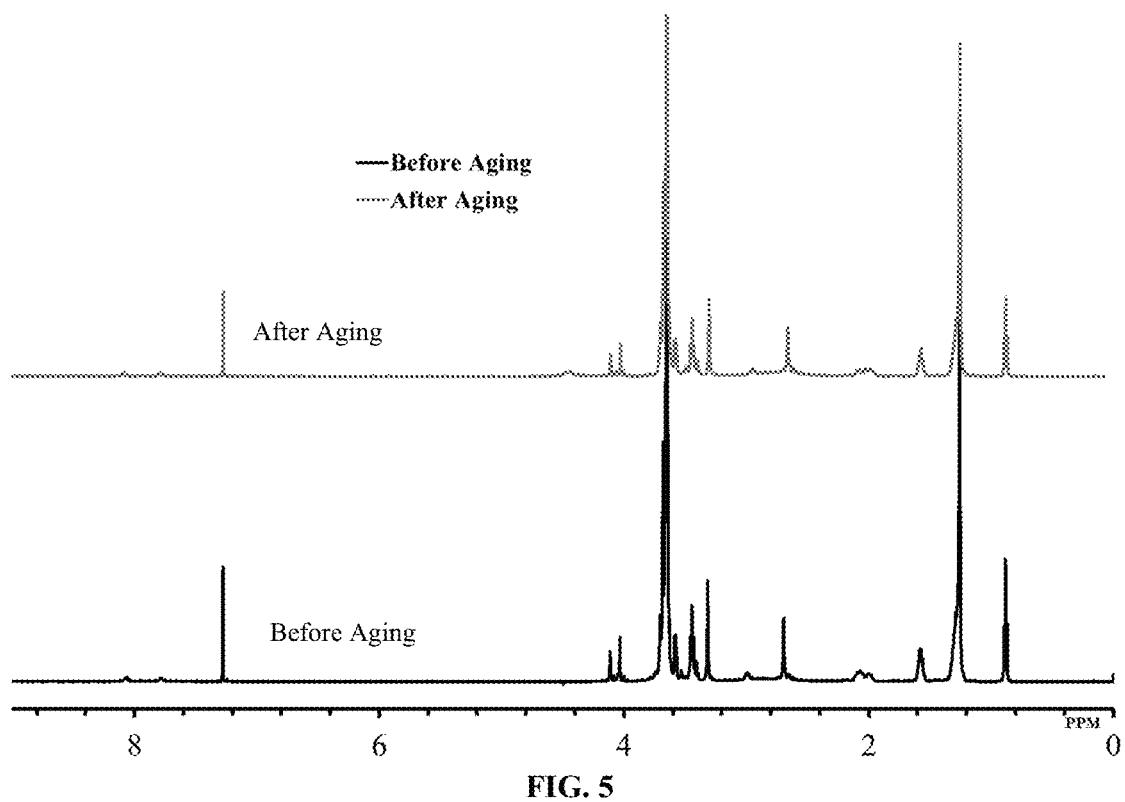
FIG. 5 is an overlay of $^1H$ NMR spectra of surfactant 12-E2-12 before and after aging at 90° C.

The surfactant of the present disclosure exhibits good thermal stability at up to a temperature of 250-320° C., preferably 270-300° C., more preferably 280-290° C. without degradation (see FIGS. 3-5), which is a temperature that is 1.5-4 times, 2-3.5 times, or 2.5-3 times as the actual reservoir temperature during oil recovery processes.

The presence of amide moiety [R—C(O)—NH—] in a surfactant structure showed several advantages including water solubility, biodegradability, low CMC, and environmentally benign [S. S. Hussain, M. S. Kamal, Effect of large spacer on surface activity, thermal, and rheological properties of novel amido-amine cationic gemini surfactants, Journal of Molecular Liquids, 242 (2017) 1131-1137, incorporated herein by reference in its entirety]. As an example, reported CMC of DTAB (with no amide group) was 16.1 mM, whereas the reported cmc of the corresponding surfactant (with amide group) was 4.4 mM [J. Hogue, P. Kumar, V. K. Aswal, J. Haldar, Aggregation properties of amide bearing cleavable gemini surfactants by small angle neutron scattering and conductivity studies, The Journal of Physical Chemistry B, 116 (2012) 9718-9726, incorporated herein by reference in its entirety].

As disclosed herein, it was observed that the incorporation of a sufficient number of ethylene oxide groups among the ionic head group and a surfactant tail into the surfactant significantly enhance its solubility [B. Barry, R. Wilson, CMC, counterion binding and thermodynamics of ethoxylated anionic and cationic surfactants, Colloid and Polymer Science, 256 (1978) 251-260, incorporated herein by reference in its entirety]. The solubility enhancement may be attributed to the hydrogen bonding among water molecules and ethylene oxide groups [C. Negin, S. Ali, Q. Xie, Most common surfactants employed in chemical enhanced oil recovery, Petroleum, 3 (2017) 197-211, incorporated herein by reference in its entirety].

In one or more embodiments, the surfactant of the present disclosure is soluble in water at a temperature of 4-90° C., 10-60° C., 20-40° C., or 25-35° C. The water may be tap water, distilled water, bidistilled water, deionized water, deionized distilled water, reverse osmosis water, and/or some other water. Most preferably the water is deionized water.

In one or more embodiments, the surfactant is soluble in a saline solution at a temperature of 4-90° C., 10-60° C., 20-40° C., or 25-35° C. Minerals contained in the saline solution used herein include, but are not limited to, sodium, calcium, magnesium, potassium, sulfate, chloride, bicarbonate, carbonate, bromide, and fluoride.

In a preferred embodiment, the saline solution is sea water having a salinity of 40,000 ppm to 80,000 ppm, preferably 50,000 ppm to 70,000 ppm, more preferably 55,000 ppm to 60,000 ppm. In one embodiment, the surfactant is soluble in natural sea water or simulated sea water having sodium present at a concentration of 5-40 g/L, 10-30 g/L, or about 18 g/L, calcium present at a concentration of 0.25-2 g/L, 0.5-1.5 g/L, or about 0.7 g/L, magnesium present at a concentration of 0.5-4 g/L, 1-3 g/L, or about 2 g/L, sulfate present at a concentration of 2-8 g/L, 3-6 g/L, or about 4 g/L, chloride at a concentration of 15-60 g/L, 20-40 g/L, or about 30 g/L, and bicarbonate present at a concentration of 0.05-0.2 g/L, 0.08-0.15 g/L, or about 0.1 g/L, each relative to a total volume of the solution.

In another preferred embodiment, the aqueous solution is formation water having a salinity of 100,000 ppm to 400,000 ppm, preferably 150,000 ppm to 300,000 ppm, more preferably 200,000 ppm to 250,000 ppm. In one embodiment, the surfactant is soluble in formation water or simulated formation water having sodium present at a concentration of 30-100 g/L, 50-80 g/L, or about 60 g/L, calcium present at a concentration of 8-40 g/L, 15-30 g/L, or about 20 g/L, magnesium present at a concentration of 1-5 g/L, 2-4 g/L, or about 2.5 g/L, sulfate present at a concentration of 0.1-1 g/L, 0.2-0.6 g/L, or about 0.4 g/L, chloride at a concentration of 60-200 g/L, 100-160 g/L, or about 130 g/L, and bicarbonate present at a concentration of 0.1-1 g/L, 0.2-0.5 g/L, or about 0.4 g/L, each relative to a total volume of the solution.

As used herein, critical micelle concentration (CMC) refers to the concentration of surfactants above which micelles form. The value of the CMC for a given dispersant in a given medium depends on temperature, pressure, and on the presence of other surface active substances and electrolytes. In one embodiment, the surfactant of formula (I) has a critical micelle concentration of $2 \times 10^{-5}$ to $1 \times 10^{-4}$ mol/L, $3 \times 10^{-5}$ to $8 \times 10^{-5}$ mol/L, or $4 \times 10^{-5}$ to $6 \times 10^{-5}$ mol/L in saline having a salinity of 10,000 ppm to 400,000 ppm, preferably 50,000 ppm to 300,000 ppm, more preferably 100,000-200,000 ppm at a temperature of 4-90° C., 10-80° C., 20-70° C., 30-60° C., or 40-50° C. In one related embodiment, the surfactant of formula (I) has a critical micelle concentration of $1 \times 10^{-5}$ to $6 \times 10^{-5}$ mol/L, $2 \times 10^{-5}$ to $5 \times 10^{-5}$ mol/L, or about $3.9 \times 10^{-5}$ mol/L in the aforementioned seawater at a temperature of 10-80° C., 20-70° C., or 30-50° C. In another related embodiment, the surfactant of formula (I) has a critical micelle concentration of $2.5 \times 10^{-5}$ to $8 \times 10^{-5}$ mol/L, $3 \times 10^{-5}$ to $6 \times 10^{-4}$ mol/L, or about $5 \times 10^{-5}$ mol/L in water, preferably deionized water at a temperature of 10-80° C., 20-70° C., or 30-50° C. (see Table 3).

The surfactant disclosed herein may decrease the surface tension between two immiscible phases and facilitate mixing (i.e. dispersing) of one phase in the other. Before reaching the CMC, the surface tension changes significantly with the concentration of the surfactant. After reaching the CMC, the surface tension remains relatively constant. In one embodiment, the surfactant of the formula (I) has a surface tension value of at least 35 mN/m, preferably 36-45 mN/m, preferably 37-40 mN/m, preferably 38-39 mN/m in the sea water or deionized water at or above the aforementioned critical micelle concentration (CMC) (see Table 3).

Figure 10:
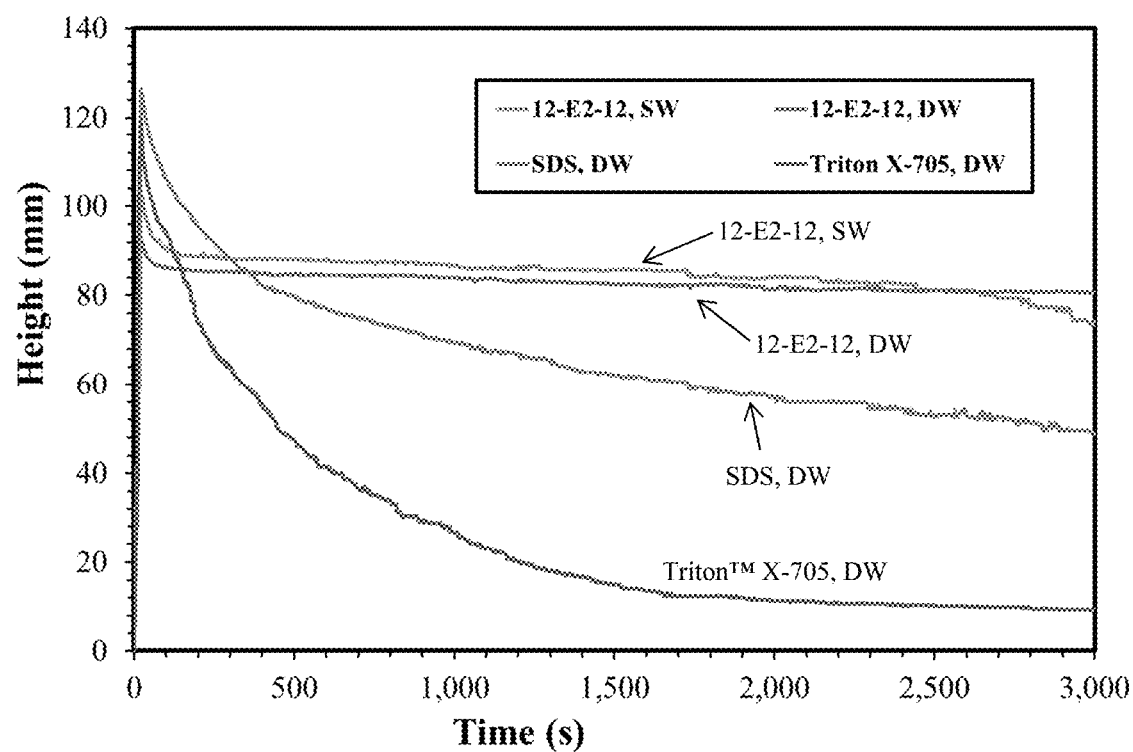
FIG. 10 is a graph comparing foam stability of surfactant 12-E2-12 in SW and DW, respectively, as well as commercial surfactants SDS (sodium dodecyl sulfate) and Triton™ X-705 in DW.
Figure 11A:
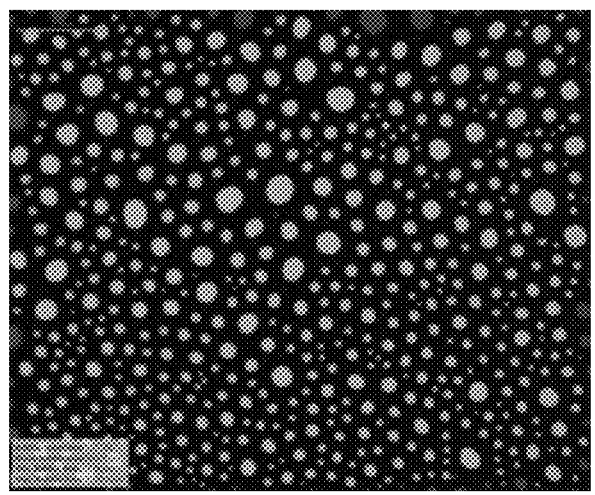
FIG. 11A is an image of foam structures at 0 min generated using 0.1 wt % surfactant 12-E2-12 in DW.
Figure 11B:
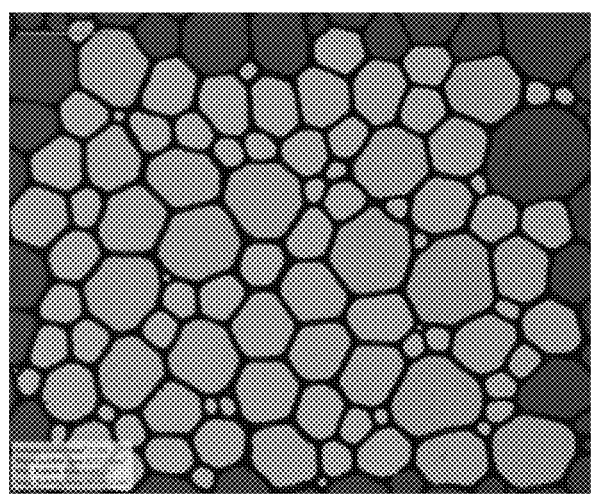
FIG. 11B is an image of foam structures at 30 min generated using 0.1 wt % surfactant 12-E2-12 in DW.
Figure 11C:
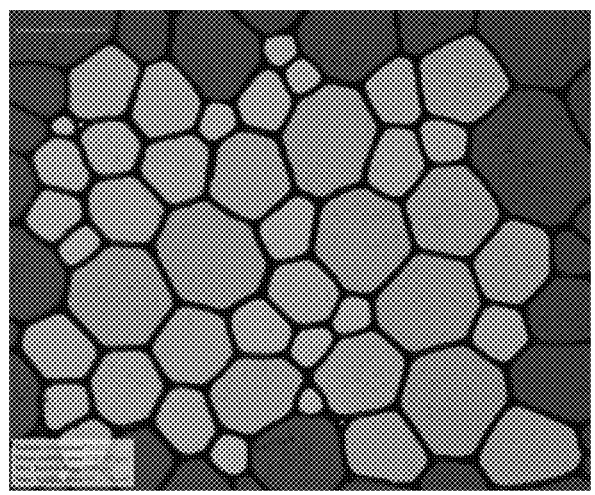
FIG. 11C is an image of foam structures at 60 min generated using 0.1 wt % surfactant 12-E2-12 in DW.
Figure 11D:
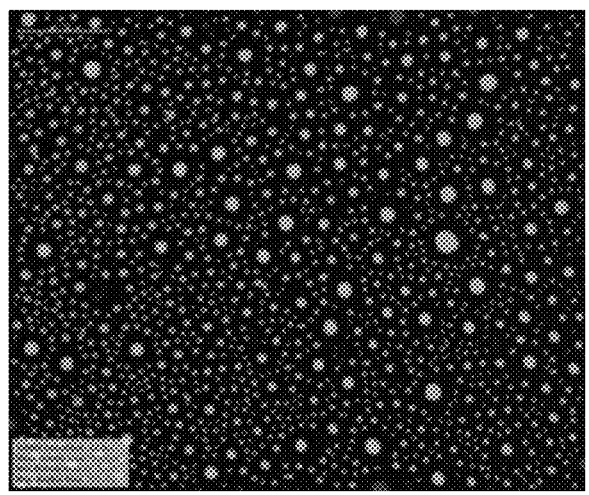
FIG. 11D is an image of foam structures at 0 min generated using 0.1 wt % surfactant 12-E2-12 in SW.
Figure 11E:
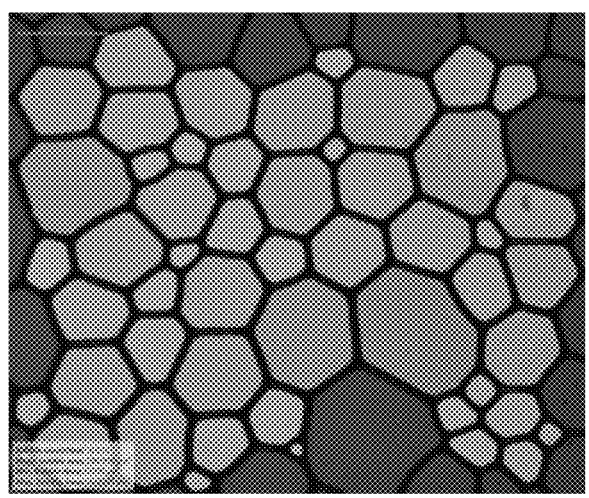
FIG. 11E is an image of foam structures at 30 min generated using 0.1 wt % surfactant 12-E2-12 in SW.
Figure 11F:
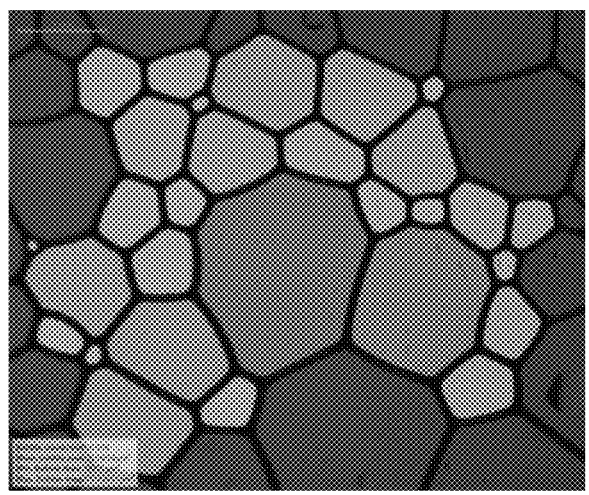
FIG. 11F is an image of foam structures at 60 min generated using 0.1 wt % surfactant 12-E2-12 in SW.
Figure 11G:
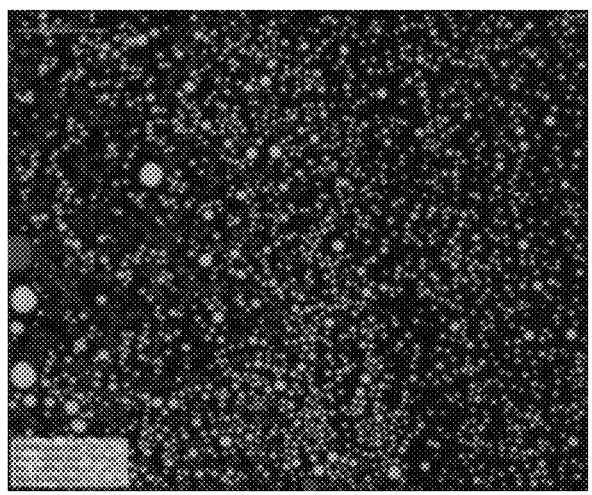
FIG. 11G is an image of foam structures at 0 min generated using 0.1 wt % commercial surfactant SDS in DW.
Figure 11H:
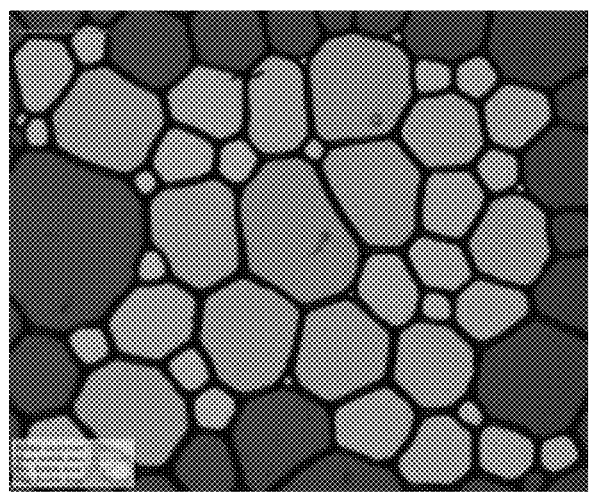
FIG. 11H is an image of foam structures at 30 min generated using 0.1 wt % commercial surfactant SDS in DW.
Figure 11I:
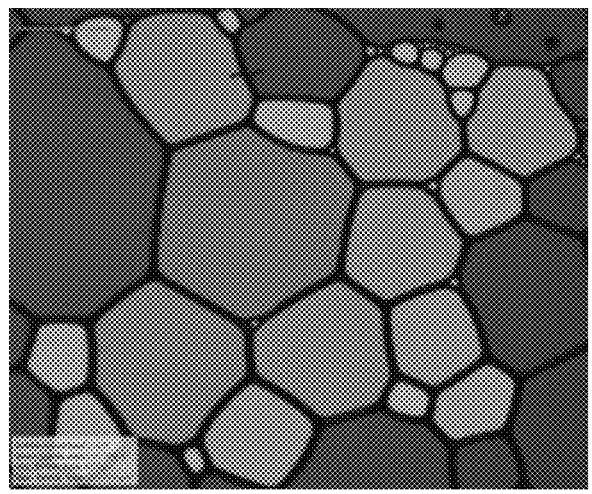
FIG. 11I is an image of foam structures at 60 min generated using 0.1 wt % commercial surfactant SDS in DW.
Figure 11J:
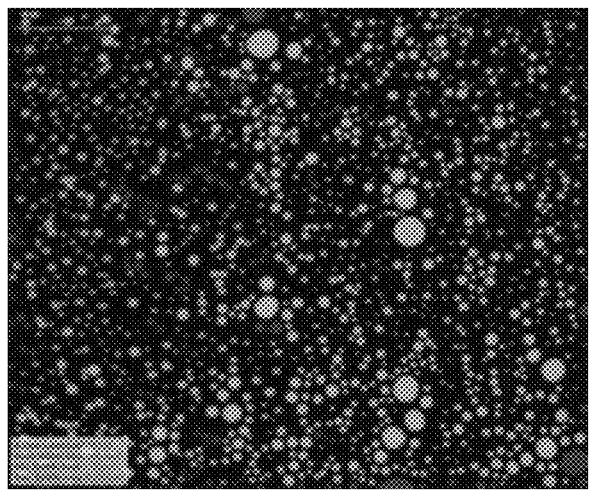
FIG. 11J is an image of foam structures at 0 min generated using 0.1 wt % commercial surfactant Triton™ X-705 in DW.
Figure 11K:
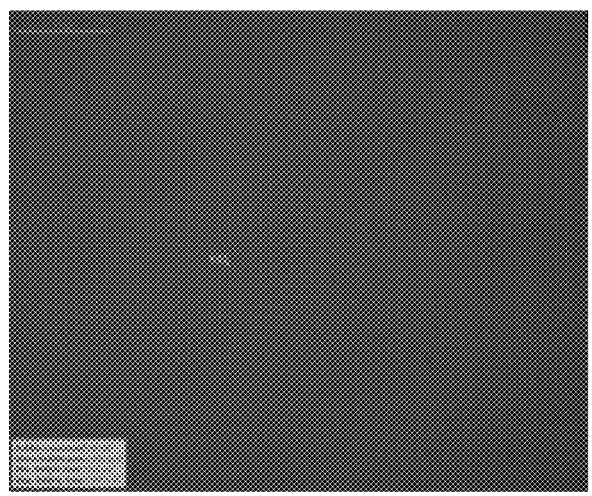
FIG. 11K is an image of foam structures at 30 min generated using 0.1 wt % commercial surfactant Triton™ X-705 in DW.
Figure 11L:
FIG. 11L is an image of foam structures at 60 min generated using 0.1 wt % commercial surfactant Triton™ X-705 in DW.

As shown in FIG. 10, the surfactant disclosed herein has superior foaming stability. Foam stability of a surfactant may be analyzed using a foam analyzer, for example, Dynamic Foam Analyzer (DFA100) manufactured by Kruss Gmbh, Germany (see Example 7). A lower foam height indicates lower foaming. In addition, a decrease in foam height after standing for a short period of time (e.g. 30 minutes, 60 minutes) indicates easily breakable and short-lived foam. In one embodiment, the foam generated by the surfactant of formula (I) in water (e.g. sea water, deionized water) shows a foam height decrease of less than 25%, preferably 5-20%, more preferably 10-15% after standing for 200-5,000 seconds, 500-3,000 seconds, or 1,000-2,000 seconds. In one related embodiment, the foam generated by the surfactant of formula (I) in water (e.g. sea water, deionized water) has a foam height decrease which is at least 50% less, preferably 55-75% less, preferably 60-70% less than that of a foam generated by a commercial surfactant SDS (sodium dodecyl sulfate) via foaming experiment performed in a substantially similar manner. In another related embodiment, the foam generated by the surfactant of formula (I) in water (e.g. sea water, deionized water) has a foam height decrease which is at least 65% less, preferably 70-85% less, preferably 75-80% less than that of a foam generated by a commercial surfactant Triton™ X-705 available from the Dow Chemical Company via foaming experiment performed in a substantially similar manner (see FIG. 10).

The surfactant of the present disclosure may be especially suitable for recovery processes of petrochemicals from reservoirs with high salinity and elevated temperature. The surfactant may be also used in formulating detergents, which can include one or more conventional additives such as buffers, abrasives, bleaching agent, brighteners, fragrances, dyes, antistatic agents, antimicrobial agents, enzymes, and the like.

According to a second aspect, the present disclosure relates to a method of recovering hydrocarbons from a reservoir. The method involves the steps of injecting a composition comprising an aqueous solution and an oil recovery formulation into the reservoir, and collecting hydrocarbons from the reservoir, wherein the oil recovery formulation contains the surfactant of formula (I) of the first aspect in any of its embodiments.

In a preferred embodiment, the surfactant used herein has the formula (II),

As used herein, monomers are molecules which can undergo polymerization, thereby contributing constitutional repeating units to the structures of a macromolecule or polymer. The process by which monomers combine end to end to form a polymer is referred to herein as "polymerization". As used herein, a "copolymer" refers to a polymer derived from more than one species of monomer and are obtained by "copolymerization" of more than one species of monomer. Copolymers obtained by copolymerization of two monomer and/or oligomer species may be termed bipolymers, those obtained from three monomers may be termed terpolymers and those obtained from four monomers may be termed quarterpolymers, etc.

The oil recovery formulation used herein may comprise at least one polymer or copolymer selected from the group consisting of a copolymer involving reacted units of acrylamide (AM) and 2-acrylamido-2-methylpropane sulfonic acid (AMPS), poly 2-acrylamido-2-methylpropane-sulfonic acid (polyAMPS), polyacrylamide, partially-hydrolyzed polyacrylamide, a terpolymer involving reacted units of acrylamide, 2-acrylamido-2-methyl-1-propanesulfonic acid, and N-vinylpyrrolidone, polymethacrylamide, and Xanthan gum.

In one embodiment, the oil recovery formulation used herein comprises the surfactant of formula (I) and a copolymer. Block copolymers comprise two or more homopolymer subunits linked by covalent bonds. The union of the homopolymer subunits may require an intermediate non-repeating subunit, known as a junction block. Block copolymers with two or three distinct blocks are called diblock copolymers and triblock copolymers, respectively. Statistical copolymers are copolymers in which the sequence of monomer residues follows a statistical rule. That is, the probability of finding a particular monomer residue at a particular point in the chain is equal to the mole fraction of that monomer residue in the chain. The statistical copolymer may be referred to as a truly random copolymer. The copolymer of the present disclosure may be a block copolymer (e.g. a block bipolymer) or a random copolymer (e.g. a random bipolymer).

Preferably, the oil recovery formulation contains a copolymer involving reacted units of acrylamide (AM) and 2-acrylamido-2-methylpropane sulfonic acid (AMPS), which is also referred to as "AM-AMPS copolymer". 2-Acrylamido-2-methylpropane sulfonic acid (AMPS) was a Trademark name by The Lubrizol Corporation. AMPS is a reactive, hydrophilic, sulfonic acid acrylic monomer used to alter the chemical properties of wide variety of anionic

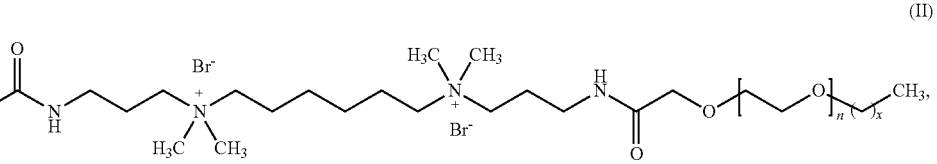

(II)

where each of n is an integer in a range of 1-15, preferably 2-14, preferably 3-13, preferably 4-12, preferably 5-11, preferably 6-10, preferably 7-9, or 8, and each of x is an integer in a range of 5-21, preferably 7-20, preferably 9-19, preferably 11-18, preferably 13-17, preferably 15-16. Most preferably, each of n is an integer in a range of 6-11, 7-10, or 8-9. For example, n is 9, 10, or 11. In a related embodiment, each of x is an integer in a range of 11-13, or 12.

polymers. AM is a water soluble monomer used to manufacture various polymers, especially polyacrylamide. Other monomers that may be incorporated in addition to or in lieu of AM to the copolymer include, but are not limited to, methacrylamide, N-methylacrylamide, N-methylmethacrylamide, diacetone acrylamide, dimethylaminopropylmethacrylamide, isopropylaminopropyl methacrylamide, acrylic acid, methacrylic acid, itaconic acid, and maleic acid.

In one or more embodiments, the copolymer has a molar ratio of acrylamide to 2-acrylamido-2-methylpropane sulfonic acid in a range of 1:10 to 10:1, preferably 1:9 to 9:1, preferably 1:8 to 8:1, preferably 1:7 to 7:1, preferably 1:6 to 6:1, preferably 1:5 to 5:1, preferably 1:4 to 4:1, preferably 1:3 to 3:1, preferably 1:2 to 2:1, preferably 2:3 to 3:2, or about 1:1.

In one or more embodiments, the copolymer used herein has a mass average molecular weight in a range of 1,000-20,000 kDa, preferably 2,000-15,000 kDa, preferably 3,000-10,000 kDa, preferably 4,000-9,500 kDa, preferably 5,000-9,000 kDa, preferably 6,000-8,500 kDa, preferably 7,000-8,000 kDa.

The copolymer of the present disclosure may be synthesized via procedures known to those of ordinary skill in the art. For example, the copolymer may be prepared through a radical polymerization of AM and AMPS using a radical initiator such as potassium persulfate. Alternatively, the copolymer used herein may be available from commercial vendors such as SNF Floerger (France).

In a preferred embodiment, the surfactant of formula (I) is present in an amount of 0.01-0.2 wt %, preferably 0.02-0.15 wt %, preferably 0.025-0.1 wt %, preferably 0.03-0.075 wt %, preferably 0.035-0.05 wt %, preferably 0.04-0.045 wt %, relative to a total weight of the composition. However, in certain embodiments, the surfactant of formula (I) may be present in an amount that is less than 0.01 wt % or greater than 0.2 wt % relative to a total weight of the composition.

In one embodiment, the copolymer is present in an amount of up to 1 wt %, preferably 0.1-0.9 wt %, preferably 0.15-0.8 wt %, preferably 0.2-0.6 wt %, preferably 0.25-0.5 wt %, preferably 0.3-0.45 wt %, preferably 0.35-0.4 wt %, relative to a total weight of the composition. However, in certain embodiments, the copolymer may be present in an amount that is less than 0.1 wt % relative to a total weight of the composition.

As used herein, the term "water injection" or "waterflooding" refers to a method of oil recovery in which water or a fluid is injected into a petroleum reservoir to sweep and displace mobile oil from a subterranean geological formation. The water injected increases pressure within the reservoir, replenishing the natural reservoir pressure that has been previously depleted in primary recovery, and physically sweeps the displaced mobile oil to adjacent production wells. Generally, the water or fluid used in a waterflooding process is taken from nearby water sources, and is usually natural seawater, fresh water, produced water (byproduct of the oil industry), aquifer water, river water, artificial saline water or brine.

The aqueous solution used herein may act as the fluid for recovering oil. In one or more embodiments, the aqueous solution is saline having a salinity of 10,000 ppm to 400,000 ppm, preferably 50,000 ppm to 300,000 ppm, more preferably 100,000-200,000 ppm. Minerals contained in saline used herein include, but are not limited to, sodium, calcium, magnesium, potassium, sulfate, chloride, bicarbonate, carbonate, bromide, and fluoride. In a preferred embodiment, the aqueous solution is sea water, or formation water as previously specified. In certain embodiments, when the aqueous solution is natural seawater, the solution may further contain microbial components and other organic pollutants that can be optionally removed prior to the oil recovery process.

"Hydrocarbons", "petroleum", "crude oil", or "oil" may be used interchangeably to refer to carbonaceous material originating from subterranean sources as well as synthetic hydrocarbon products, including organic liquids or gases, kerogen, bitumen, crude oil, natural gas or from biological processes, that is principally hydrogen and carbon, with significantly smaller amounts (if any) of heteroatoms such as nitrogen, oxygen and sulfur, and, in some cases, also containing small amounts of metals. Crude oil (e.g., liquid petroleum) and natural gas (e.g., gaseous petroleum) are both hydrocarbons.

As used herein, the terms "reservoir", "oil reservoir" and "petroleum reservoir" refer to a component of a petroleum system (i.e. hydrocarbon or petroleum-generating and storing geologic system) that is composed of a subsurface body of rock formations having sufficient porosity and permeability to store and transmit fluids. Sedimentary rocks are the most common reservoir rocks because they have more porosity than most igneous and metamorphic rocks and form under temperature conditions at which hydrocarbons can be preserved. Depending on the type of sedimentary rock, reservoirs can be classified as carbonate reservoirs having predominantly limestones, and sandstone reservoirs having primarily siliclastic rocks and clay. In one embodiment, the reservoir is a carbonate reservoir, or a sandstone reservoir. Alternatively, the reservoir is a tight shale reservoir formed by hydraulic fracturing.

As used herein, the terms "bore" and "wellbore" refer to a drilled hole or borehole of a reservoir, including the open hole or uncased portion of the well. In some embodiments, a borehole refers to the inside diameter of the wellbore wall, the rock face that bounds the drilled hole. Depending on the embodiment, a wellbore can be used for injection, production, or both.

The present disclosure provides a method of recovering hydrocarbons from a petroleum reservoir. The method involves injecting the composition containing the aforementioned aqueous solution and oil recovery formulation including, for example, the surfactant of formula (I) and the copolymer comprising reacted units of acrylamide and 2-acrylamido-2-methylpropane sulfonic acid into the reservoir, and collecting hydrocarbons from the reservoir.

The step of recovering hydrocarbons may be performed by injecting the composition into a first wellbore (e.g. an injection wellbore) connected to the reservoir and then collecting hydrocarbons from a second wellbore (e.g. a production wellbore) that is connected to the reservoir. Alternatively, the method may be performed by injecting the composition into a wellbore connected to the reservoir, and then collecting hydrocarbons from the same wellbore. Injection pressures and flow rates of the composition may be kept constant or varied. In one embodiment, the injection pressure of the composition is up to 5,000 psi, preferably 50-3,000 psi, preferably 100-1,000 psi. In a related embodiment, the injection flow rate of the composition is 0.1-50 mL/min, preferably 0.5-20 mL/min, preferably 1-10 mL/min.

In some embodiments, the composition for injection is prepared by pre-mixing the surfactant of formula (I) and the copolymer with the aqueous solution that is taken from nearby water sources or prepared on site during oil recovery operations prior to the injection. In an alternative embodiment, the oil recovery formulation (e.g. the surfactant of formula (I) and the copolymer) may be injected simultaneously with the aqueous solution, such as seawater, formation water, and produced water, into the reservoir in an amount sufficient to produce the composition in situ. In another alternative embodiment, components of the oil recovery formulation may be injected sequentially (e.g. the copolymer is injected after the injection of the surfactant of formula (I)) with the aqueous solution into the reservoir.

The hydrocarbons may be collected and separated from the injected drilling fluid at a fluids processing facility using fluids separation reagents such as emulsion breakers and water clarifiers.

In one or more embodiments, the reservoir has a temperature of 50-310° C., 75-280° C., 100-250° C., or 150-200° C. The reservoir may have a pressure of 100-3,000 psi, 200-2,500 psi, 400-2,000 psi, 800-1,500 psi, or 1,000-1,200 psi. The oil recovery formulation used herein may substantially increase the yield of hydrocarbons from underground reservoirs when injected and are particularly useful for increasing yield of hydrocarbons in reservoirs comprising high temperature water sources, high salinity water sources, or high temperature/high salinity water sources.

The examples below are intended to further illustrate protocols for preparing, characterizing the surfactant of formula (I), the composition, and uses thereof, and are not intended to limit the scope of the claims.

Example 1

Materials

The gemini cationic surfactants (12-E1-12 and 12-E2-12) were synthesized in house using a procedure described in FIG. 1 [S. S. Hussain, M. S. Kamal, Effect of large spacer on surface activity, thermal, and rheological properties of novel amido-amine cationic gemini surfactants, Journal of Molecular Liquids, 242 (2017) 1131-1137; and S. S. Hussain, M. S. Kamal, B. El Ali, A. S. Sultan, Synthesis and Evaluation of Novel Amido-Amine Cationic Gemini Surfactants Containing Flexible and Rigid Spacers, Journal of Surfactants and Detergents, 20 (2017) 777-788, each incorporated herein by reference in their entirety]. Glycolic acid ethoxylate lauryl ether (average $M_n$~690), glycolic acid ethoxylate lauryl ether (average $M_n$~360, 98%), 3-(dimethylamino)-1-propylamine (99%), NaF (≥99%), 1,6-dibromohexane (96%), and aluminum oxide (99.99%) were acquired from sigma Aldrich through local vendors. AM-AMPS copolymer containing 25% degree of anionicity with a molecular weight of 8 million Dalton was received from SNF Floerger (France). All salts for the preparation of FW and SW such as $Na_2SO_4$, $CaCl_2$, $MgCl_2$, NaCl, $NaHCO_3$ were obtained from Aldrich company. The ionic compositions of FW and SW are shown in Table 1.

TABLE 1

| Salt composition of FW and SW | | |
|---|---|---|
| Ions | FW (g/L) | SW (g/L) |
| Sodium | 59.5 | 18.3 |
| Calcium | 19.1 | 0.7 |
| Magnesium | 2.5 | 2.1 |
| Sulfate | 0.4 | 4.3 |
| Chloride | 132.1 | 32.2 |
| Bicarbonate | 0.4 | 0.1 |
| Total | 214 | 57.7 |

Example 2

Chemical Structure Elucidation

The chemical structures of the synthesized surfactants 12-E1-12 and 12-E2-12, as well as their intermediates, were elucidated by proton (500 MHz) and carbon (125 MHz) NMR and FT-IR spectra. NMR technique was performed on a Joel 1500 spectrometer using chloroform-d as the solvent, and tetramethylsilane (TMS) as an internal standard, and ppm scale was used to record the data. FT-IR technique was conducted on a Perkin-Elmer FT-IR spectrometer (16F model) and the FT-IR data was recorded in $cm^{-1}$.

Example 3

Thermogravimetric Analysis (TGA)

SDT Q600 equipment from TA apparatus was used to acquire TGA spectra using temperature scanning rate of 20° $C. \cdot min^{-1}$. The temperature range was set from 30° C. to 500° C., and the nitrogen flow was kept constant at 100 $mL \cdot min^{-1}$.

Example 4

Solubility Test 10 wt % solutions of 12-E1-12 and 12-E2-12 were made in DW, SW, FW, respectively, and placed in an oven at the reservoir temperature (90° C.) for 90 days. The solubility was monitored during this 90-day period.

Example 5

Surface Tension Analysis

A force tensiometer (Biolin Scientific) was used to analyze surface tension values via du Noüy ring method. The ring was rinsed with water and then burnt red hot on a blue flame to check for proper cleanliness of the container and the ring. The surface tensions were measured at 30° C.

Example 6

Rheology Measurement

Rheological experiments were performed on a DHR-3 rheometer from TA Instruments. The experiments were conducted using DIN concentric cylinder geometry with 28 cm bob diameter and 30.43 cm cup diameter. Steady shear rheology analysis was performed at 80° C. and 0.001-1000 (1/s) shear range. Dynamic shear rheology analysis was performed at 80° C. using a frequency range of 0.1-100 rad/s and 10% strain.

Example 7

Foam Stability

Foam analysis was performed using a DFA 100 foam analyzer (Kruss GmbH, Germany). A filter paper with a pore size of 16-40 μm was placed in the filter paper holder. The filter paper holder was then placed in a measuring column holder. A sample volume of 50 mL was placed carefully into the column with a syringe and a long needle. A measuring column with a prism was attached to the holder with the filter paper holder at the center. The LED and light sensors were 1 mm apart from the measuring column to ensure accurate foam height detection. A middle field of view set on the camera was used to get bubbles of intermediate sizes. Camera calibration was done with the dots imprinted at the top of the prism. The camera height was then set at 85 cm with the aid of the meter rule on the equipment to be close to the foam-liquid interface after calibration. Foam generation was done for 20 s using flowing air through the filter paper at a rate of 0.2 L/min.

Example 8

Synthesis of Intermediates 3a and 3b

The intermediates were synthesized according to the procedure outlined in FIG. 1 [Z. Chu, Y. Feng, A facile route towards the preparation of ultra-long-chain amidosulfobetaine surfactants, Synlett, 2009 (2009) 2655-2658, incorporated herein by reference in its entirety]. The reaction between 3-(dimethylamino)-1-propylamine (4) (11.35 g, 111.11 mmol) and glycolic acid ethoxylate lauryl ether (average $M_n$~360) (5a) (20 g, 55.56 mmol) using sodium fluoride (0.23 g, 5.56 mmol) as a catalyst was performed in a 250 mL reaction flask. The reaction was conducted in the presence of argon for six hours at 160° C. using $Al_2O_3$ to absorb the water produced during the reacting. Afterward, additional 3-(dimethylamino)-1-propylamine (8.52 g, 83.33 mmol) was added to the reaction mixture and the experiment was progressed for an additional six hours. After that, unreacted 3-(dimethylamino)-1-propylamine was removed and the residue was treated with cold acetone followed by drying under vacuum to obtain intermediate 3a.

Intermediate 3b was synthesized using the same synthetic procedure starting with glycolic acid ethoxylate lauryl ether (average $M_n$~690) (5b).

Ethoxylated Alkyl Amidopropyl-N-N-Dimethylamine 3a:

Yellow viscous material. $^1$H-NMR (CDCl$_3$, 500 MHz, δ in ppm): 0.87 (CH$_3$, t, J=6.7 Hz), 1.14-1.34 ((CH$_2$)$_n$, m), 1.52-1.62 (CH$_2$, m), 1.70 (CH$_2$, t, J=6.9 Hz), 2.24 ((CH$_3$)$_2$, s), 2.37 (CH$_2$, t, J=7.0 Hz), 3.29-3.39 (m, CH$_2$), 3.46 (C$_2$, t, J=7.0 Hz), 3.58 (C$_2$, m), 3.60-3.73 ((—O—CH$_2$—CH$_2$—)$_n$, m,), 3.90 (CH$_2$, s), 7.54 (NH, s).

Ethoxylated Alkyl Amidopropyl-N-N-Dimethylamine 3b:

Pale yellow viscous oil. $^1$H-NMR (CDCl$_3$, 500 MHz, δ in ppm): 0.87 (CH$_3$, t, J=6.7 Hz), 1.16-1.36 ((CH$_2$)$_n$, m), 1.51-1.61 (CH$_2$, m), 1.69 (CH$_2$, t, J=6.9 Hz), 2.22 ((CH$_3$)$_2$, s), 2.34 (CH$_2$, t, J=7.0 Hz), 3.30-3.40 (CH$_2$, m), 3.45 (CH$_2$, t, J=7.0 Hz), 3.57 (CH$_2$, m), 3.60-3.72 ((—O—CH$_2$—CH$_2$—)$_n$, m), 3.99 (CH$_2$, s), 7.57 (NH, s).

Example 9

Synthesis of Cationic Poly(Ethylene Oxide) Gemini Surfactant (12-E1-12)

The intermediate 3a (10.0 g, 22.54 mmol) and 1,6-dibromohexane 2 (2.20 g, 9.02 mmol) were refluxed in dry ethanol (10 mL) for 2 days (FIG. 1). The resulting crude product was purified by flash column using ethanol as a mobile phase to obtain surfactant 12-E1-12 as a waxy solid [R. Zana, M. Benrraou, R. Rueff, Alkanediyl-.alpha.omega.-bis (dimethylalkylammonium bromide) surfactants. 1. Effect of the spacer chain length on the critical micelle concentration and micelle ionization degree, Langmuir, 7 (1991) 1072-1075, incorporated herein by reference in its entirety].

Surfactant 12-E2-12 was synthesized using the same synthetic procedure starting with the intermediate 3b.

Cationic Poly(Ethylene Oxide) Gemini Surfactant (12-E1-12)

Waxy solid. $^1$H NMR (CDCl$_3$, 500 MHz, δ in ppm): 0.88 (2×CH$_3$, t, J=6.7 Hz), 1.15-1.35 ((CH$_2$)$_n$, m), 1.48-1.55 (2×CH$_2$, m), 1.55-1.62 (2×H$_2$, m), 1.84-1.90 (2×CH$_2$, m), 2.03-2.09 (2×CH$_2$, m), 3.23 (4×CH$_3$, s), 3.49-3.76 (m, (—O—CH$_2$—CH$_2$—)$_n$), 4.03 (2×CH$_2$, m), 7.95 (2×NH, s). $^{13}$C NMR (CDCl$_3$, 125 MHz, δ in ppm): 14.0, 21.7, 22.6, 23.0, 26.0, 29.2, 29.4, 29.7, 31.8, 35.9, 51.1, 62.0, 64.2, 69.9-71.9, 171.0.

FTIR (ν in cm$^{-1}$) 3405 ($ν_{N-H}$), 2923 ($ν_{C-H}$ asymmetric), 2854 ($ν_{C-H}$ symmetric), 1653 (amide [I]), 1542 (amide [II]), 1466, 1348, 1251, 1110 (C—O—C stretching vibration), 947 [A. K. Ghumare, B. V. Pawar, S. S. Bhagwat, Synthesis and antibacterial activity of novel amido-amine-based cationic gemini surfactants, Journal of Surfactants and Detergents, 16 (2013) 85-93].

Cationic Poly(Ethylene Oxide) Gemini Surfactant (12-E2-12)

Waxy solid. $^1$H NMR (CDCl$_3$, 500 MHz, δ in ppm): 0.88 (2×CH$_3$, t, J=6.7 Hz, (CH$_3$)$_2$), 1.16-1.36 ((CH$_2$)$_n$, m), 1.47-1.67 (4 x CH$_2$, m), 1.85-1.91 (2×CH$_2$, m), 2.01-2.08 (2×CH$_2$, m), 3.22 (4×CH$_3$, s), 3.48-3.75 (m, (OCH$_2$CH$_2$)$_n$), 4.03 (2×CH$_2$, m), 7.99 (2×NH). $^{13}$C NMR (CDCl$_3$, 125 MHz, δ in ppm): 14.0, 21.7, 22.5, 23.0, 26.0, 29.3, 29.4, 29.6, 31.8, 35.9, 51.1, 62.1, 64.4, 69.9-71.5, 171.1.

FTIR (ν in cm$^{-1}$) 3397 ($ν_{N-H}$), 2923 ($ν_{C-H}$ asymmetric), 2853 ($ν_{C-H}$ symmetric), 1651 (amide [I]), 1544 (amide [II]), 1466, 1348, 1250, 1108 (C—O—C stretching vibration), 947 [A. K. Ghumare, B. V. Pawar, S. S. Bhagwat, Synthesis and antibacterial activity of novel amido-amine-based cationic gemini surfactants, Journal of Surfactants and Detergents, 16 (2013) 85-93].

Example 10

Results and Discussion: Synthesis

Synthetic procedure of cationic poly(ethylene oxide) gemini surfactants 12-E1-12 and 12-E2-12 containing different degrees of ethoxylation was depicted in FIG. 1 [Z. Chu, Y. Feng, A facile route towards the preparation of ultra-long-chain amidosulfobetaine surfactants, Synlett, 2009 (2009) 2655-2658; and R. Zana, M. Benrraou, R. Rueff, Alkanediyl-αΩ,Ω-bis (dimethylalkylammonium bromide) surfactants. 1. Effect of the spacer chain length on the critical micelle concentration and micelle ionization degree, Langmuir, 7 (1991) 1072-1075, each incorporated herein by reference in their entirety]. Compound 4 (3-(dimethyl-amino)-1-propylamine) was reacted with compound 5a in the presence of NaF at 160° C. to achieve the intermediate 3a. In the second step, 3a was reacted with 2 (1,6-dibromo-hexane) to acquire the desired cationic poly(ethylene oxide) gemini surfactant 1a (12-E1-12). The other surfactant 1b (12-E2-12) containing a higher degree of ethoxylation was synthesized using the same synthetic procedure starting with the intermediate 5b.

Example 11

Results and Discussion: Structure Elucidation

Structures were elucidated using proton and carbon NMR as well as FT-IR spectroscopies. The structure elucidation of 12-E2-12 was presented herein as an example. According to $^{13}$C-NMR spectrum of 12-E2-12 (FIG. 4), the methyl and methylene groups of the surfactant tail were detected at δ 14.1 ppm and δ 22.6-35.9 ppm, respectively. The $CH_3$ moieties associated with the quaternary ammonium head groups [—(CH$_3$)$_2$—N—(CH$_2$)$_6$—N—(CH$_3$)$_2$-] could be coupled with the peak detected at δ 51.1 ppm. Similarly, methylene moieties connected to the ammonium head groups [—CH$_2$—N—(CH$_3$)$_2$—CH$_2$—(CH$_2$)$_4$—CH$_2$—(CH$_3$)$_2$—N—CH$_2$—] could be assigned to peaks at δ62.1 ppm and δ64.4 ppm. Methylene moieties of the ethylene oxide chain (—CH$_2$—CH$_2$—O—CH$_2$—CH$_2$—O—) could be assigned to the overlapping signals at δ70.0-71.5 ppm [A. Bodin, M. Linnerborg, J. L. G. Nilsson, A.-T. Karlberg, Structure elucidation, synthesis, and contact allergenic activity of a major hydroperoxide formed at autoxidation of the ethoxylated surfactant C12E5, Chemical research in toxicology, 16 (2003) 575-582]. The signals detected at δ 171.1 ppm represented the amide group [—CH$_2$—C=O—NH—].

In $^1$H-NMR spectrum of 12-E2-12 (FIG. 5), the signals at δ0.88 ppm and δ1.15-1.35 ppm could be associated with the terminal CH$_3$ and CH$_2$ moieties [(CH$_3$—(CH$_2$)$_n$—] of the hydrophobic tail, respectively. The signals at δ 3.22 ppm represented the CH$_3$ moieties of the quaternary ammonium head groups [—(CH$_3$)$_2$—N—(CH$_2$)$_6$—N—(CH$_3$)$_2$—] [N. Pal, N. Saxena, A. Mandal, Studies on the physicochemical properties of synthesized tailor-made gemini surfactants for application in enhanced oil recovery, Journal of Molecular Liquids, 258 (2018) 211-224]. The CH$_2$ moieties of ethylene oxide chain (—CH$_2$—CH$_2$—O—CH$_2$—CH$_2$—O—) could be coupled with the overlapping signals at δ3.59-3.70 ppm [A. Bodin, M. Linnerborg, J. L. G. Nilsson, A.-T. Karlberg, Structure elucidation, synthesis, and contact allergenic activity of a major hydroperoxide formed at autoxidation of the ethoxylated surfactant C12E5, Chemical research in toxicology, 16 (2003) 575-582]. The signals at δ4.03 ppm could be assigned to CH$_2$ groups connected to the carbonyl carbon [—O—CH$_2$—C=O—NH—]. The signals at δ7.99 ppm could be assigned to the amide group [—O—CH$_2$—C=O—NH—].

Figure 6:
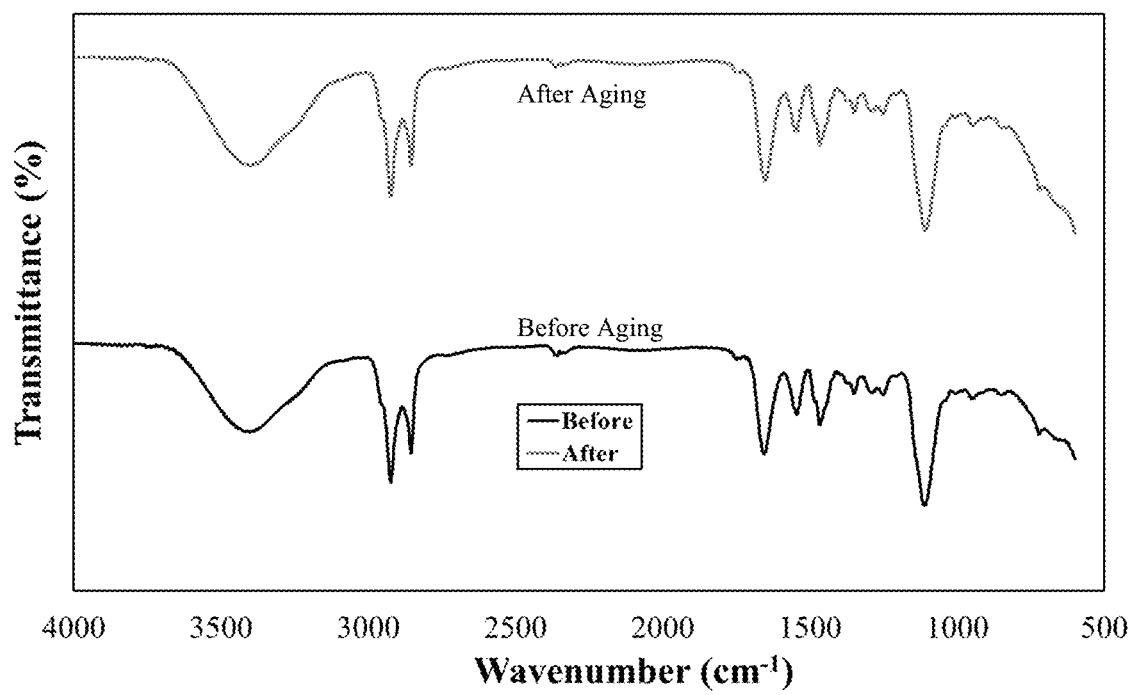
FIG. 6 is an overlay of FTIR spectra of surfactant 12-E2-12 before and after aging at 90° C.

In FTIR spectra (FIG. 6), adsorption peak at 3397 cm$^{-1}$ corresponded to NH stretching. Characteristic adsorption bands at 2923 cm$^{-1}$, as well as 2853 cm$^{-1}$, corresponded to stretching vibration of C—H in the surfactant tail. The stretching vibration of both amides was observed at 1651 cm$^{-1}$ and 1544 cm$^{-1}$, respectively. The C—H bending vibration was exhibited by an adsorption band at 1466 cm$^{-1}$, while the stretching band of C—O—C groups was observed at 1108 cm$^{-1}$. Accordingly, the proton and carbon NMR, as well as FT-IR spectra, matched well with the proposed structure of the surfactant 12-E2-12.

Example 12

Results and Discussion: Solubility and Salt Resistance

The stability of injected surfactant at elevated oilfield temperatures in the presence of various ions, as well as solubility in injected water (SW) and oilfield water (FW), is a prerequisite for the surfactant to be applicable in petroleum industry. Previously, the poor solubility of the surfactant containing long hydrophobic tail (≥C18) was observed and hence not appropriate for oil and gas applications [S. Shakil Hussain, M. A. Animashaun, M. S. Kamal, N. Ullah, I. A. Hussein, A. S. Sultan, Synthesis, characterization and surface properties of amidosulfobetaine surfactants bearing odd-number hydrophobic tail, Journal of Surfactants and Detergents, 19 (2016) 413-420, incorporated herein by reference in its entirety].

Figure 2A:
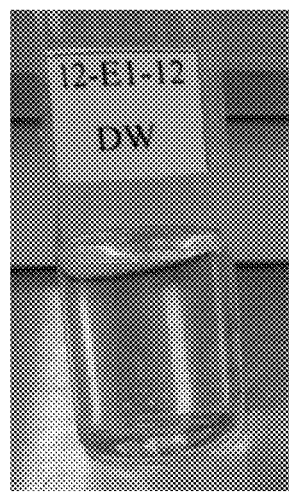
FIG. 2A is a picture showing a solution of surfactant 12-E1-12 in deionized water (DW).
Figure 2B:
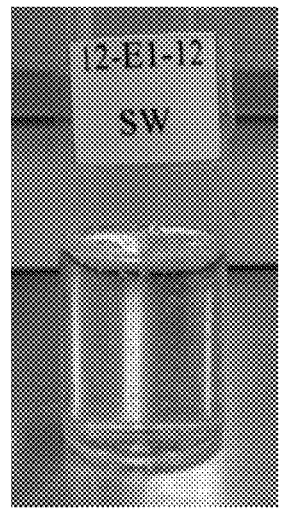
FIG. 2B is a picture showing a solution of surfactant 12-E1-12 in sea water (SW).
Figure 2C:
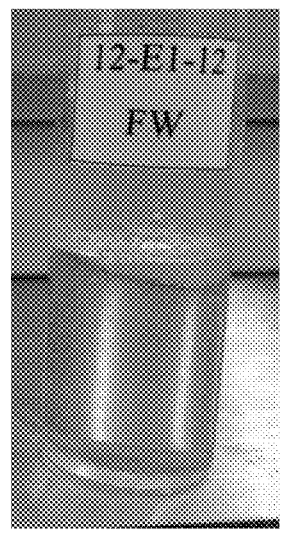
FIG. 2C is a picture showing a solution of surfactant 12-E1-12 in formation water (FW).
Figure 2D:
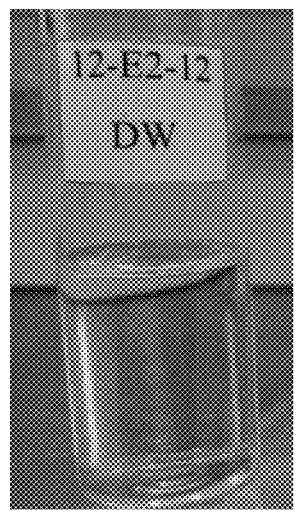
FIG. 2D is a picture showing a solution of surfactant 12-E2-12 in DW.
Figure 2E:
FIG. 2E is a picture showing a solution of surfactant 12-E2-12 in SW.
Figure 2F:
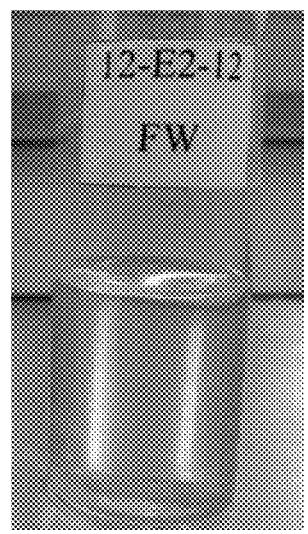
FIG. 2F is a picture showing a solution of surfactant 12-E2-12 in FW.

The solubility and salt tolerance tests of 12-E1-12 and 12-E2-12 were conducted at reservoir temperature (90° C.) in FW, SW, and DW, respectively, for 90 days. The salt composition of FW and SW is summarized in Table 1. The solubility results are outlined in Table 2. The surfactant 12-E1-12 with a fewer number of ethylene oxide units showed poorer solubility in FW and SW (FIGS. 2B-C). However, the surfactant with a greater number of ethylene oxide units showed more satisfactory solubility in all types of water tested (FIGS. 2D-F). Solutions of 12-E2-12 in DW, SW, and FW stayed clear at 90° C. for 90 days without showing any precipitation or phase separation. Furthermore, structure elucidation results (NMR and FTIR) (FIGS. 4-6) confirmed the excellent stability of 12-E2-12 after the aging.

TABLE 2

| The solubility of 12-E1-12 and 12-E2-12 at room temperature | | | |
|---|---|---|---|
| Surfactants | DW | SW | FW |
| 12-E1-12 | Transparent | Precipitation | Severe precipitation |
| 12-E2-12 | Transparent | Transparent | Transparent |

Example 13

Results and Discussion: Heat Stability

In surfactant flooding, a surfactant stays in the oilfield for several days or months at a temperature greater than 90° C. Therefore, both short-term and long-term heat stabilities of the surfactant 12-E2-12 were investigated using TGA analysis and aging method, respectively.

As shown in the TGA graph of 12-E2-12 (FIG. 3), an initial loss of about 25% in weight was observed due to evaporation of organic solvents and water. A significant decomposition was observed at 314° C., which indicated great heat stability of the surfactant 12-E2-12.

The long-term heat stability of 12-E2-12 was investigated using the aging technique in which 10 wt % of 12-E2-12 was added to SW and DW, respectively in separate vials. The vials were left in the oven at 90° C. for 3 months. The samples were then taken out and subjected to NMR and FT-IR analysis after the aging.

The NMR and FT-IR studies of the aged samples indicated that 12-E2-12 showed good stability and no structure decomposition after the aging. In $^{13}$C NMR spectra of the aged sample of 12-E2-12 (FIG. 4), the appearance of methyl and methylene moieties of the surfactant tail were detected by the signals at δ 14.1 ppm and 22.6-35.9 ppm, respectively. The signals at δ 51.1 ppm indicated the existence of $CH_3$ moieties connected with the quaternary ammonium head groups. Similarly, methylene moieties directly attached to the quaternary ammonium head groups were also observed at δ 62.1 ppm and δ 64.4 ppm. The overlapping peaks at δ70.0-71.5 ppm indicated the existence of ethylene oxide groups [—$\underline{C}H_2$—$\underline{C}H_2$—O—$\underline{C}H_2$—$\underline{C}H_2$—O—]. The peak at δ171.1 indicated the occurrence of the amide group. According to $^1$H NMR data (FIG. 5) of the aged sample of 12-E2-12, the existence of methyl and methylene moieties of surfactant tail were observed by the signals at δ 0.88 ppm and δ1.16-1.36 ppm. Signals at δ 3.22 ppm indicated the presence of $CH_3$ moieties associated with the quaternary ammonium head groups. The overlapping peaks at δ 3.48-3.75 ppm revealed the existence of ethylene oxide groups [—$C\underline{H}_2$—$C\underline{H}_2$—O—$C\underline{H}_2$—$C\underline{H}_2$—O—]. The broad peak at δ 7.99 ppm indicated the occurrence of the amide group. According to FT-IR results (FIG. 6) of the aged sample of 12-E2-12, the signals at 3405 cm$^{-1}$ indicated the presence of the amide. The signals observed at 2853 cm$^{-1}$ and 2923 cm$^{-1}$ showed the existence of aliphatic C—H stretching. The amide I and amide II bands at 1654 cm$^{-1}$ and 1542 cm$^{-1}$, respectively were also observed. Moreover, the stretching mode of the ether moieties [—$CH_2$—$CH_2$—O—$CH_2$—$CH_2$—O—] was detected at 1110 cm$^{-1}$. Accordingly, proton and carbon NMR, as well as FT-IR spectra of the aged sample of 12-E2-12 matched well with the proposed structure of 12-E2-12.

Example 14

Results and Discussion: Surface Tension

Figure 7:
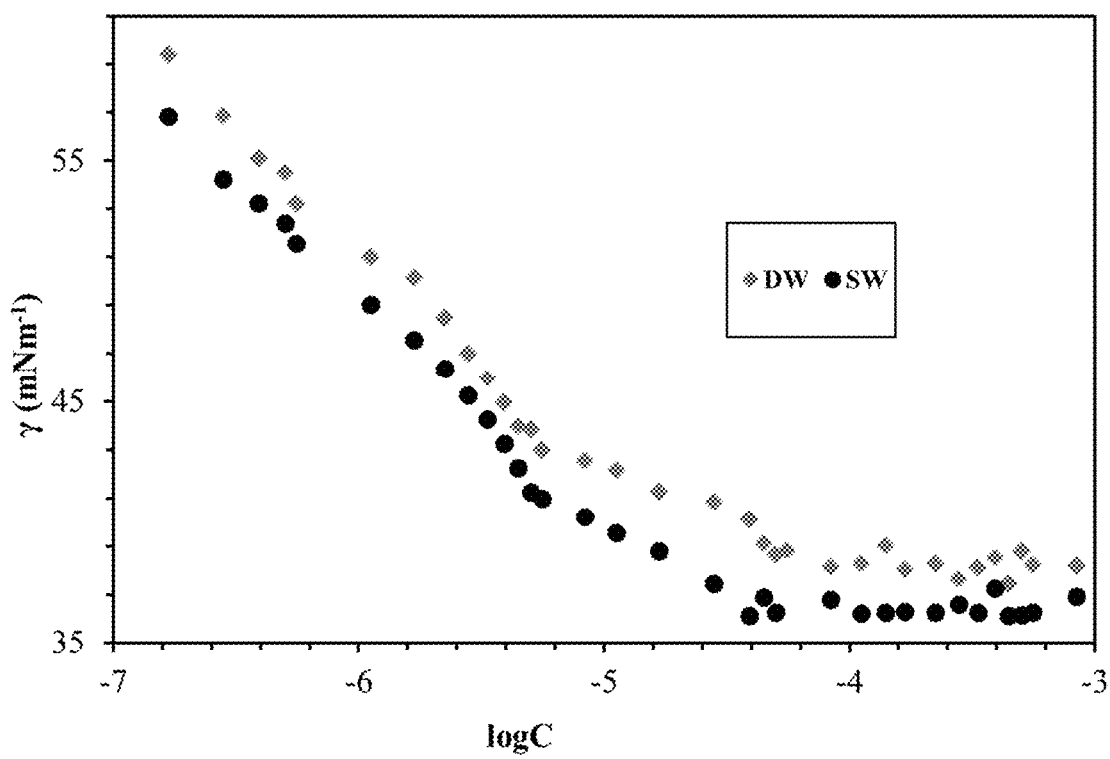
FIG. 7 is an overlay of surface tension of surfactant 12-E2-12 at different log of concentration measured at 30° C. in DW, and SW, respectively.

Surface tension and other surface properties of the surfactant were evaluated using deionized water and synthetic seawater, respectively at a controlled temperature environment (30° C.). FIG. 7 is a plot showing the surface tension of 12-E2-12 against its concentration logarithm. Other surface properties calculated using the surface tension data include cmc and surface tension at cmc) ($\gamma_{cmc}$), maximum surface access ($r_{max}$), surfactant ability to lower surface tension ($\pi_{cmc}$), and per molecule minimum area ($A_{min}$). Surface parameters were calculated based on the following equations, $$\pi_{cmc} = \gamma_0 - \gamma_{cmc} \quad (1)$$

$$\Gamma_{max} = -\frac{1}{nRT}\left(\frac{d\gamma}{d\ln C}\right)_T \quad (2)$$

$$A_{min} = 10^{18}/N_A\Gamma_{max} \quad (3)$$

where $\gamma_0$ represents DW surface tension, dγ/dlnC represents gradient below cmc, R represents gas constant, C represents the concentration of surfactant, T is the temperature, $N_A$ represents Avogadro number, and n=3 for such type of gemini surfactant.

The reduction in surface tension was noticed upon enhancing the concentration of the surfactant till the cmc was attained. The surface tension was almost constant at concentrations higher than cmc. At a given concentration, the surface tension of the surfactant in seawater was lower compared to the surface tension in deionized water. A similar trend in surface tension reduction with increasing salinity was noted for ethoxylated zwitterionic surfactants [S. S. Hussain, L. T. Fogang, M. S. Kamal, Synthesis and performance evaluation of betaine type zwitterionic surfactants containing different degrees of ethoxylation, J. Mol. Struct., DOI (2018), incorporated herein by reference in its entirety]. The cmc and $\gamma_{cmc}$ were extracted by the plot of surface tension against concentration. Both parameters (cmc and $\gamma_{cmc}$) of the surfactant reduced with an increase in salinity.

Surface tension reduction usually depends on surfactant adsorption at the interface. Any factors that increase the tendency of the surfactant to adsorb more can decrease the surface tension. Salts usually help the polar group to adsorb more by reducing hydration. Also, salts addition leads to tighter packing at the air-water interface due to reduced repulsion between the surfactant polar groups, which may result in lower cmc and $\gamma_{cmc}$ of gemini cationic surfactants upon addition of salts. A slight reduction in maximum surface access was observed with enhancing water salinity. The addition of salts resulted in increasing value of $A_{min}$ from 2.83 nm$^2$ to 3.12 nm$^2$. In summary, the synthesized surfactant showed excellent surface properties and low cmc, which is an important parameter of consideration when selecting a surfactant for oilfield applications.

TABLE 3

Surface properties of the synthesized surfactant

| Type of water | cmc (mol/L) | $\gamma_{cmc}$ (mN/m) | $\pi_{cmc}$ (mN/m) | $\Gamma_{max} \times 10^6$ (mol/m$^2$) | $A_{min}$ (nm$^2$) |
|---|---|---|---|---|---|
| DW | 5.02 × 10$^{-5}$ | 38.66 | 33.34 | 0.58 | 2.83 |
| SW | 3.91 × 10$^{-5}$ | 36.12 | 35.08 | 0.53 | 3.12 |

Example 15

Results and Discussion: Rheology

Figure 8:
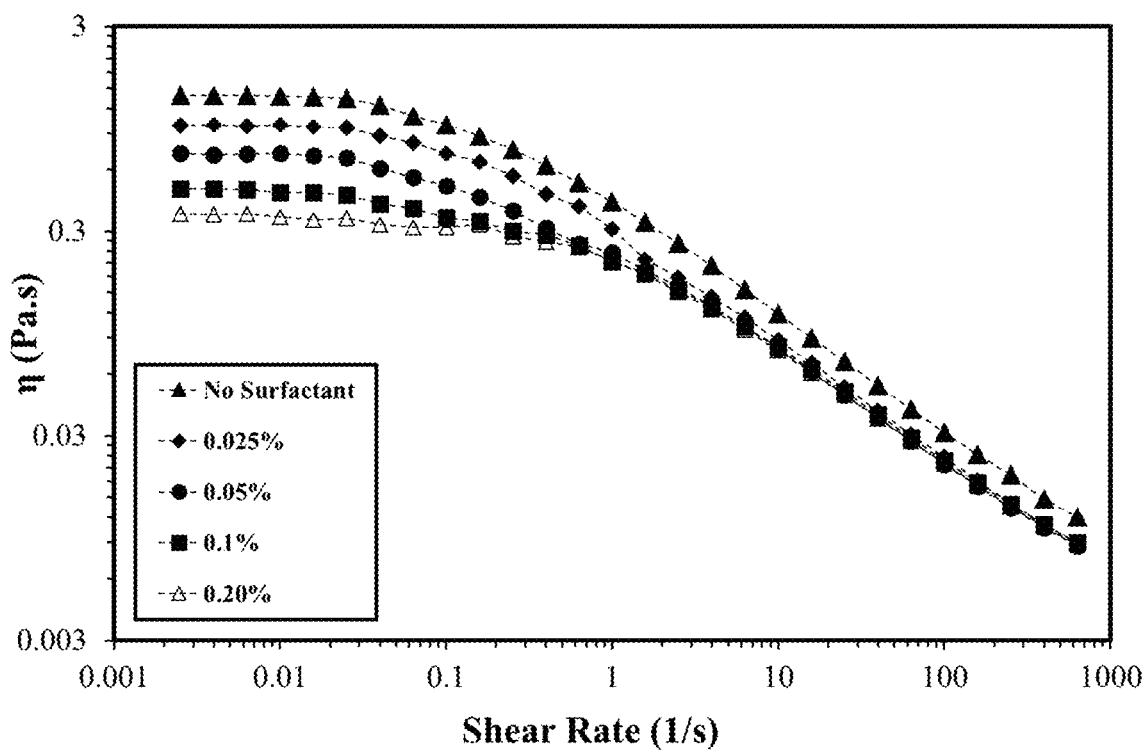
FIG. 8 shows steady shear viscosity of the oil recovery formulation containing the copolymer and surfactant 12-E2-12 in different concentrations.

The understanding of surfactant-polymer interactions is important for designing formulations for chemical enhanced oil recovery. The interactions between a surfactant and a polymer could significantly affect the rheological properties and displacing characteristics of the polymer injected. The interactions between the surfactant disclosed herein with polymer were measured by steady shear and dynamic rheology by varying the concentration of the surfactants. FIG. 8 showed the impact of surfactant concentration on polymer viscosity at various shear rates.

At low shear rates, the increase in the concentration of the surfactant significantly decreased polymer viscosity. However, at high shear rates, the impact of surfactant concentration on the polymer viscosity was not significant. In DW, the increase in polymer viscosity was observed as a result of polymer chain stretching due to charge repulsion. However, counter ions (anions) resulting from the addition of 12-E2-12 could interact with the cations present on the polymer chain. These interactions resulted in the coiling of the polymer chain, which ultimately reduced the viscosity. Viscosity reduction was linked to the surfactant-polymer interactions as well as applied shear. Major reduction in the viscosity was observed when the shear rate was low due to insignificant impact of shear. However, at elevated shear rates, the influence of shear was found to be dominant as compared with charge interactions. Hence, similar viscosity values were noted for surfactant-polymer solutions at elevated shear rates.

Figure 9:
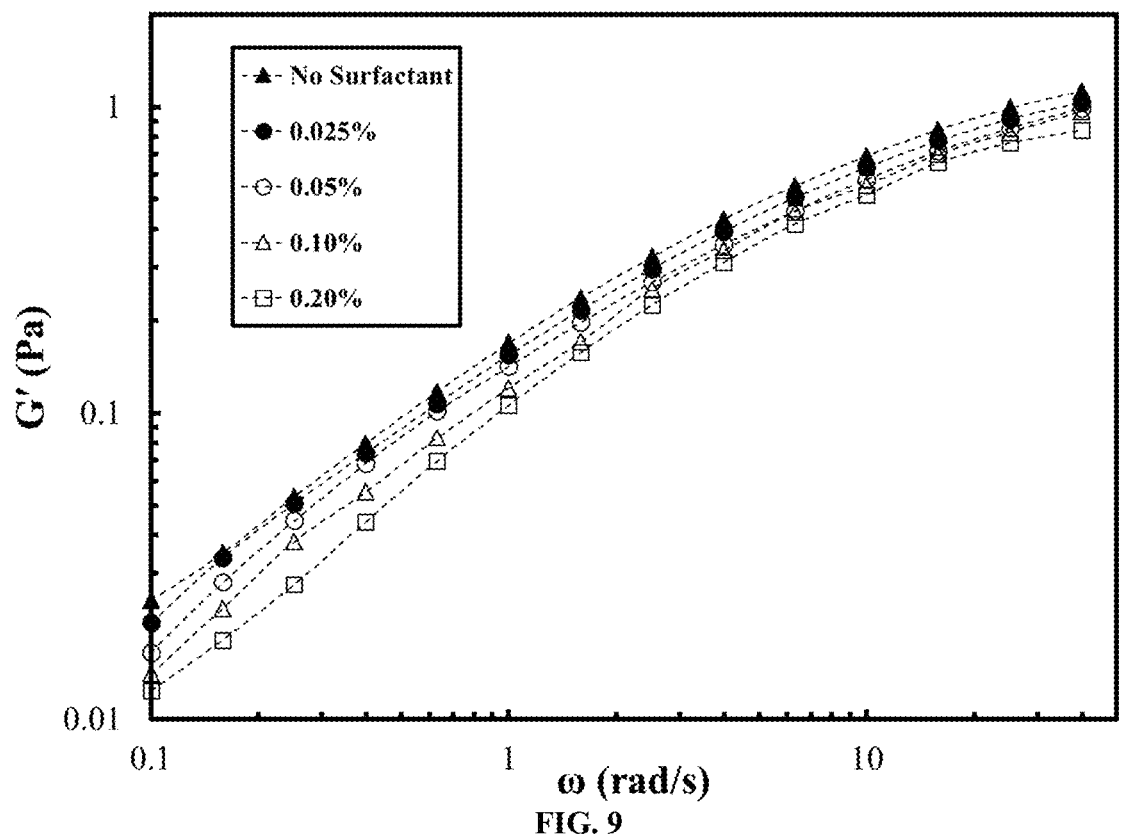
FIG. 9 shows storage modulus of the oil recovery formulation containing the copolymer and surfactant 12-E2-12 in different concentrations.

Polymer elasticity is an important parameter and recent literature had shown that polymers with higher elasticity led to improved oil recovery [T. S. Urbissinova, J. J. Trivedi, E. Kuru, Effect of elasticity during viscoelastic polymer flooding: A possible mechanism of increasing the sweep efficiency, SPE Western Regional Meeting, 27-29 May, Anaheim, Calif., USA, Socoiety of Petroleum Engineers, 2010; and Z. Zhang, J. Li, J. Zhou, Microscopic Roles of "Viscoelasticity" in HPMA polymer flooding for EOR, Transport. Porous. Med., 86 (2011) 199-214, each incorporated herein by reference in their entirety]. The change in storage modulus by varying the concentration of surfactant was assessed (FIG. 9). Polymer storage modulus decreased with increasing concentration of surfactant. This trend was more significant at lower frequency. The reduction in storage modulus by varying concentration of surfactant was also associated with the charge screening. In summary, both storage modulus and viscosity reduction were observed by increasing the concentration of the surfactant at low frequency and low shear rates, respectively. However, polymer viscosity was almost unchanged by increasing concentration of the surfactant at elevated shear rates. Further, when the polymer was dissolved in seawater, the polymer viscosity stayed almost unchanged by increasing surfactant concentration.

Example 16

Results and Discussion: Foam Stability

The foamability and foam stability are two important properties to evaluate the performance of surfactants for foaming applications. The comparison of foam stability of the synthesized surfactant and two commercial surfactants are given in FIG. 10. All measurements were conducted at a fixed surfactant concentration (0.1%) at ambient temperature. The foamability of the synthesized surfactants was slightly smaller compared to the commercial surfactants. However, the foam stability was significantly higher compared to both commercial surfactants. The initial foam generated using commercial surfactants attained a height of 120 mm, while the foam generated using the presently synthesized surfactant attained a height of 90 mm. However, the foam generated using commercial surfactants was not stable and decayed fast. The foam generated using the synthesized surfactant was much more stable compared to the commercial surfactants. The structures of foam bubbles are given in FIGS. 11A-L. The foam generation of the synthesized surfactant was slightly better when dissolved in the SW compared to the foam generated when dissolved in deionized water. This is evident from FIGS. 10A-F as the foam height of the surfactant 12-E2-12 was greater in SW than in DW. Foam height is generally affected by the number of surfactant molecules present in the solution.

The number of surfactant molecules should be the same because the surfactant concentrations were the same. Thus this effect may be due to the fact that increasing salinity readily promotes adsorption of surfactant molecules, thus increasing foam formation. Foam stability decreases with increasing salinity. This can be seen from the fact that the foam goes below the camera height. This is generally attributed to the reduction of repulsion between head groups and the density of the solution. SW has a higher density than deionized water. An increase in density increases the rate of drainage in between the bubbles, leading to a faster coalescence of the bubbles, and subsequently a collapse in foam height. Electrostatic repulsion that exists between the head groups of the surfactant molecules in deionized water was reduced because of the presence of salts. This drives the bubbles to be brought together and thus coalescence.

Example 17

The current disclosure demonstrates that surfactant stability at high reservoir temperature and solubility in oil field water can be increased by incorporating a sufficient number of EO units between the hydrophobic tail and ionic head groups. Cationic poly(ethylene oxide) gemini surfactants with fewer and greater numbers of ethylene oxide units within the framework were synthesized and examined.

The chemical structures of the surfactants were elucidated by NMR and FT-IR analysis. The surfactant containing a fewer number of ethylene oxide groups (12-E1-12) was observed to precipitate in formation water (FW) and sea water (SW). However, the surfactant with a greater number of ethylene oxide groups (12-E2-12) showed excellent solubility in deionized water (DW), SW, and FW. Therefore, the thermal, surface, rheological, and foaming properties of 12-E2-12 were further explored.

TGA analysis revealed great short-term thermal stability of 12-E2-12 and no chemical degradation was observed below 314° C., which is much higher than the existing oilfields temperature (≥90° C.). The aging experiment further demonstrated the excellent long-term heat stability of the surfactant 12-E2-12. The decrease in cmc of 12-E2-12 was observed upon enhancing salinity. Rheological tests of 12-E2-12 demonstrated that the storage modulus and polymer viscosity were reduced upon increasing concentration of the surfactant at low share rate. However, at high share rate, the influence of surfactant concentration was insignificant. Moreover, the surfactant 12-E2-12 exhibited superior foaming properties compared to commercial surfactants. The excellent physicochemical properties of the synthesized surfactant 12-E2-12 make it a promising candidate for oilfield applications at high temperature/high salinity conditions.

The invention claimed is:

1. A surfactant of formula (I)

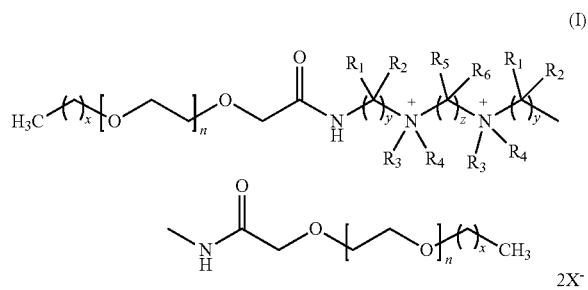

or a solvate thereof, a tautomer thereof, a stereoisomer thereof, or a mixture thereof;

wherein:

each of $R_1$ and $R_2$, and $R_5$ and $R_6$ are independently selected from the group consisting of a hydrogen, an optionally substituted alkyl, and an optionally substituted cycloalkyl;

each of $R_3$ and $R_4$ are independently selected from the group consisting of an optionally substituted alkyl, and an optionally substituted cycloalkyl;

each of n is an integer in a range of 1-15;

each of x is an integer in a range of 5-21;

each of y is an integer in a range of 2-5;

z is an integer in a range of 4-12; and

X is an anion selected from the group consisting of a halide ion; a hexafluorophosphate ion a trifluoromethanesulfonate ion, and a tetrafluoroborate ion.

2. The surfactant of claim 1, wherein each of $R_1$ and $R_2$ are independently a hydrogen, or a methyl.

3. The surfactant of claim 1, wherein each of $R_1$ and $R_2$ are a hydrogen.

4. The surfactant of claim 1, wherein each of $R_3$ and $R_4$ are independently selected from the group consisting of a methyl, an ethyl, and an isopropyl.

5. The surfactant of claim 1, wherein each of $R_3$ and $R_4$ are a methyl.

6. The surfactant of claim 1, wherein $R_5$ and $R_6$ are independently a hydrogen, or a methyl.

7. The surfactant of claim 1, wherein $R_5$ and $R_6$ are a hydrogen.

8. The surfactant of claim 1, wherein each of n is an integer in a range of 2-11.

9. The surfactant of claim 1, wherein each of x is an integer in a range of 11-13.

10. The surfactant of claim 1, wherein each of y is 3.

11. The surfactant of claim 1, wherein z is 6.

12. The surfactant of claim 1, wherein X is bromide.

13. The surfactant of claim 1, which has a formula (II)

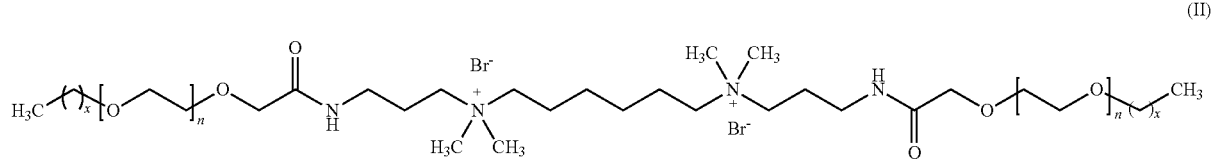

wherein:

each of n is an integer in a range of 2-11; and each of x is an integer in a range of 11-13.

14. The surfactant of claim 1, which has a critical micelle concentration of $2\times10^{-5}$ to $1\times10^{-4}$ mol/L, in saline having a salinity of 10,000 ppm to 400,000 ppm at a temperature of 20-70° C.

15. A method of recovering hydrocarbons from a reservoir, the method comprising:

injecting a composition comprising an aqueous solution and an oil recovery formulation into the reservoir; and collecting hydrocarbons from the reservoir, wherein:

the oil recovery formulation comprises:

the surfactant of claim 1; and a copolymer comprising reacted units of acrylamide and 2-acrylamido-2-methylpropane sulfonic acid.

16. The method of claim 15, wherein the copolymer has a molar ratio of acrylamide to 2-acrylamido-2-methylpropane sulfonic acid in a range of 1:10 to 10:1, and a mass average molecular weight in a range of 1,000-20,000 kDa.

17. The method of claim 15, wherein the surfactant has the formula (II)

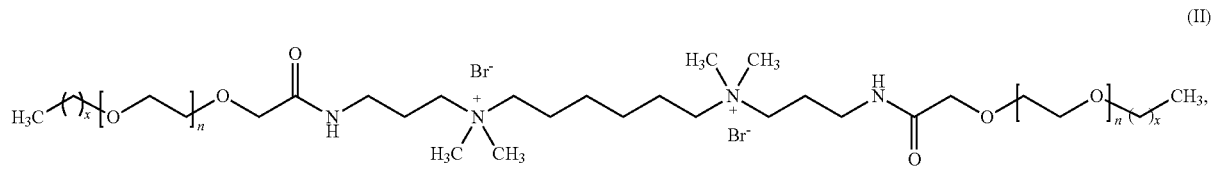

(II)

and wherein each of n is an integer in a range of 6-11, and each of x is an integer in a range of 11-13.

18. The method of claim 15, wherein the surfactant is present in an amount of 0.01-0.2 wt % relative to a total weight of the composition.

19. The method of claim 15, wherein the reservoir has a temperature of 50-310° C.

20. The method of claim 15, wherein the aqueous solution is saline having a salinity of 10,000 ppm to 400,000 ppm.

* * * * *